(12) United States Patent
Zhu et al.

(10) Patent No.: US 11,013,816 B2
(45) Date of Patent: May 25, 2021

(54) ANTIBODY DRUG CONJUGATES HAVING DERIVATIVES OF AMATOXIN AS THE DRUG

(71) Applicant: Sorrento Therapeutics, Inc., San Diego, CA (US)

(72) Inventors: Tong Zhu, San Diego, CA (US); Hong Zhang, San Diego, CA (US); Alisher B. Khasanov, San Diego, CA (US); Gang Chen, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 147 days.

(21) Appl. No.: 15/609,858

(22) Filed: May 31, 2017

(65) Prior Publication Data

US 2017/0340750 A1    Nov. 30, 2017

Related U.S. Application Data

(60) Provisional application No. 62/343,825, filed on May 31, 2016.

(51) Int. Cl.
| | |
|---|---|
| *A61K 47/68* | (2017.01) |
| *C07K 16/32* | (2006.01) |
| *C07K 7/64* | (2006.01) |
| *C07K 14/415* | (2006.01) |
| *C07K 19/00* | (2006.01) |
| *A61K 39/00* | (2006.01) |

(52) U.S. Cl.
CPC ...... *A61K 47/6831* (2017.08); *A61K 47/6851* (2017.08); *A61K 47/6855* (2017.08); *A61K 47/6857* (2017.08); *A61K 47/6863* (2017.08); *A61K 47/6883* (2017.08); *A61K 47/6889* (2017.08); *C07K 7/64* (2013.01); *C07K 14/415* (2013.01); *C07K 16/32* (2013.01); *C07K 19/00* (2013.01); *A61K 2039/505* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 9,233,173 B2 | 1/2016 | Faulstich et al. | |
| 9,884,126 B2 * | 2/2018 | Brown | A61K 31/4375 |
| 2015/0105540 A1 | 4/2015 | Miao et al. | |
| 2015/0160192 A1 | 6/2015 | Chen et al. | |

FOREIGN PATENT DOCUMENTS

| | | |
|---|---|---|
| WO | WO 2010/115629 A1 | 10/2010 |
| WO | WO 2012/041504 A1 | 4/2012 |
| WO | 2014/043403 * | 3/2014 |
| WO | WO2016001485 A1 | 1/2016 |
| WO | WO2016004043 A1 | 1/2016 |

OTHER PUBLICATIONS

Santi et al (PNAS, 109(16):6211-6216, 2012).*
Kuhn, "The Design and Synthesis of Small-Molecule Anticancer Agents Targeted Through Antibody-Drug Conjugates", A Thesis Submitted to the Faculty of Baylor University in Partial Fulfillment of the Requirements for the Honors Program, May 2014, pp. 1-86.
International Search Report for International Application No. PCT/US2017/035206 dated Oct. 18, 2017, 4 pages.
Extended European Search Report for International Application No. PCT/US2017/035206 dated Mar. 13, 2020, 7 pages.

* cited by examiner

*Primary Examiner* — Patricia Duffy
(74) *Attorney, Agent, or Firm* — McNeill Baur PLLC

(57) ABSTRACT

There is disclosed derivatives of amanitin conjugated to a targeting antibody to form an ADC (antibody drug conjugate).

17 Claims, 11 Drawing Sheets

Figure 1 - continued
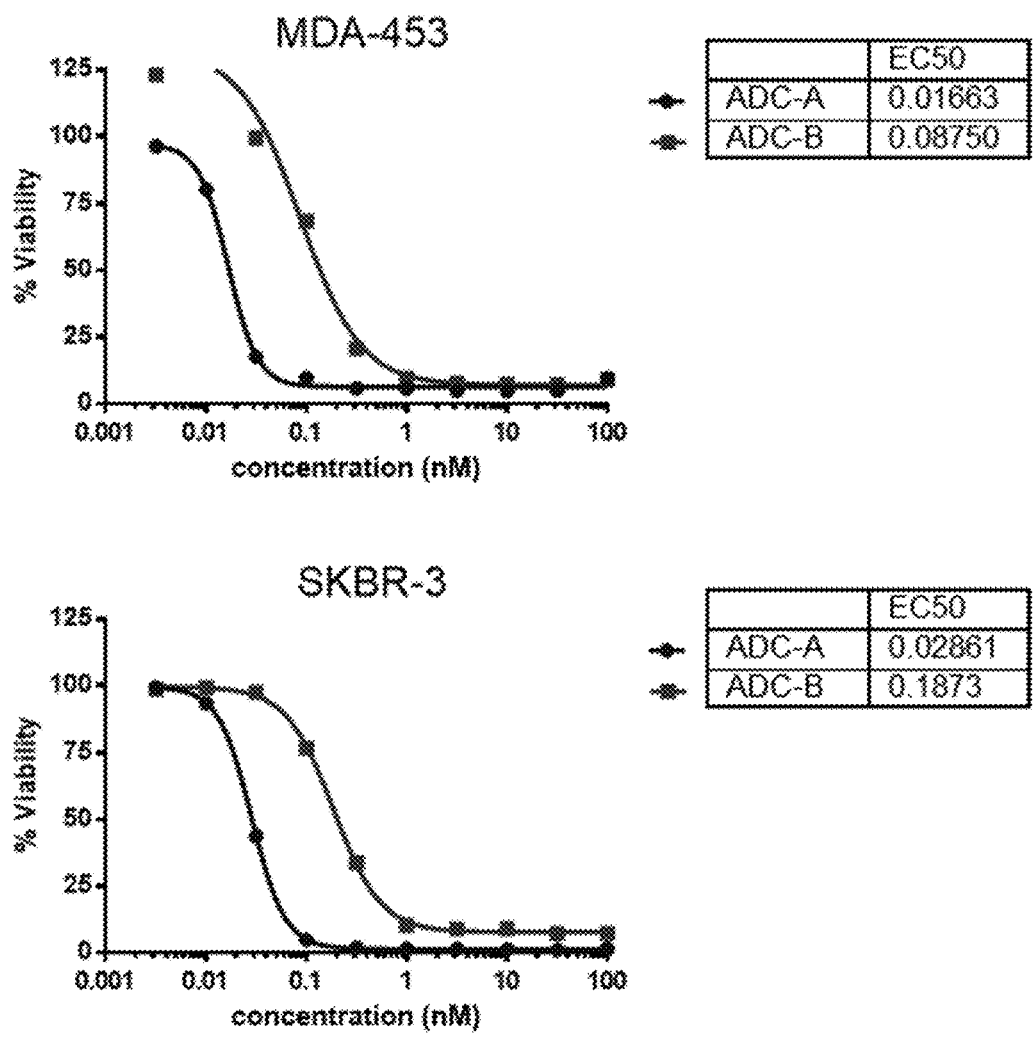

* p<0.05. One way ANOVA, multiple comparisons compared to Control group.

* p<0.05. One way ANOVA, multiple comparisons compared to Control group.

\* P < 0.05, \*\* P < 0.01, One Way Anova with post hoc Dunnett's multiple comparison test to vehicle, N=7

ANTIBODY DRUG CONJUGATES HAVING DERIVATIVES OF AMATOXIN AS THE DRUG

CROSS REFERENCE TO RELATED APPLICATION

This patent application claims priority to U.S. provisional patent application 62/343,825, filed May 31, 2016, the contents of which are incorporated herein by reference.

TECHNICAL FIELD

The present disclosure provides derivatives of amanitin conjugated to a targeting antibody to form an ADC (antibody drug conjugate).

BACKGROUND

The amatoxins are rigid bicyclic peptides having eight amino acid units. These compounds are isolated from a variety of mushroom species (e.g., *Amanita phalloides* (also known as green death cap mushroom), *Galerina marginata, Lepiota brunneo-incamata*) or are prepared synthetically. Different mushroom species contain varying amounts of different Amatoxin family members. A member of this family, alpha-amanitin, is known to be an inhibitor of eukaryotic RNA polymerase II (EC2.7.7.6) and to a lesser degree, RNA polymerase III, thereby inhibiting transcription and protein biosynthesis. Wieland (1983) Int. *J. Pept. Protein Res*. 22(3):257-276. Alpha-amanitin binds non-covalently to RNA polymerase II and dissociates slowly, making enzyme recovery unlikely. Prolonged inhibition of transcription is thought to induce cellular apoptosis.

Exemplary amatoxins include

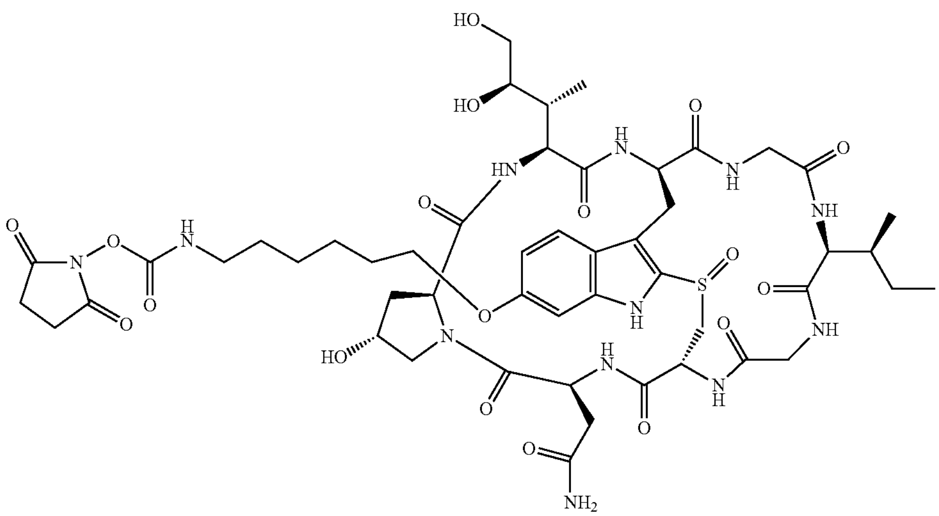

;

WO2012/041504

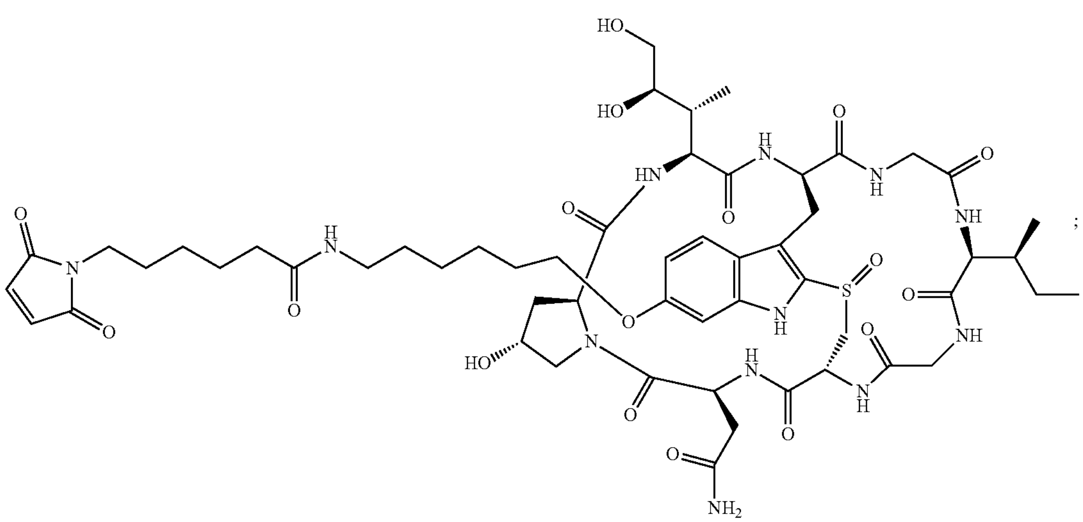

;

-continued
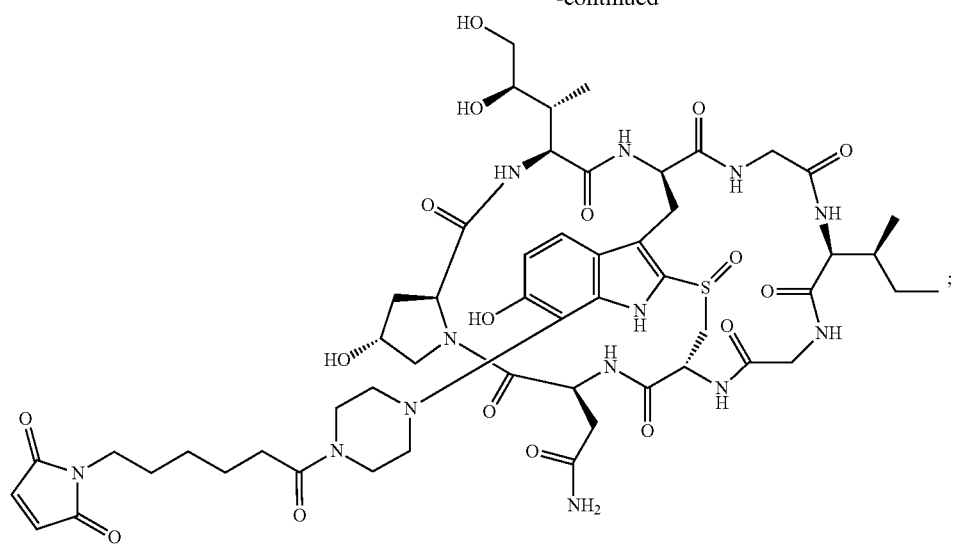
WO2014/043403
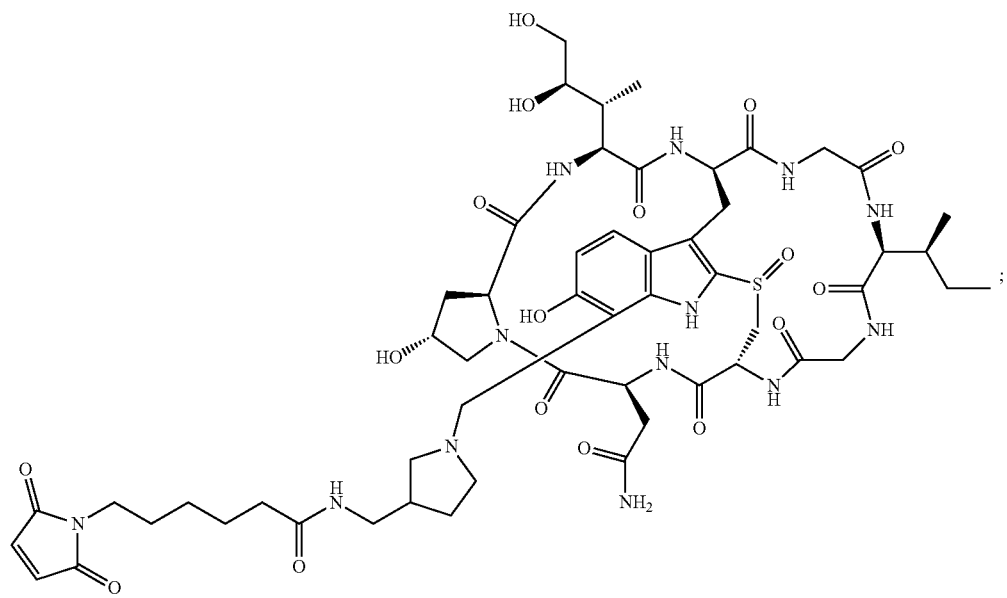
(Example 79)
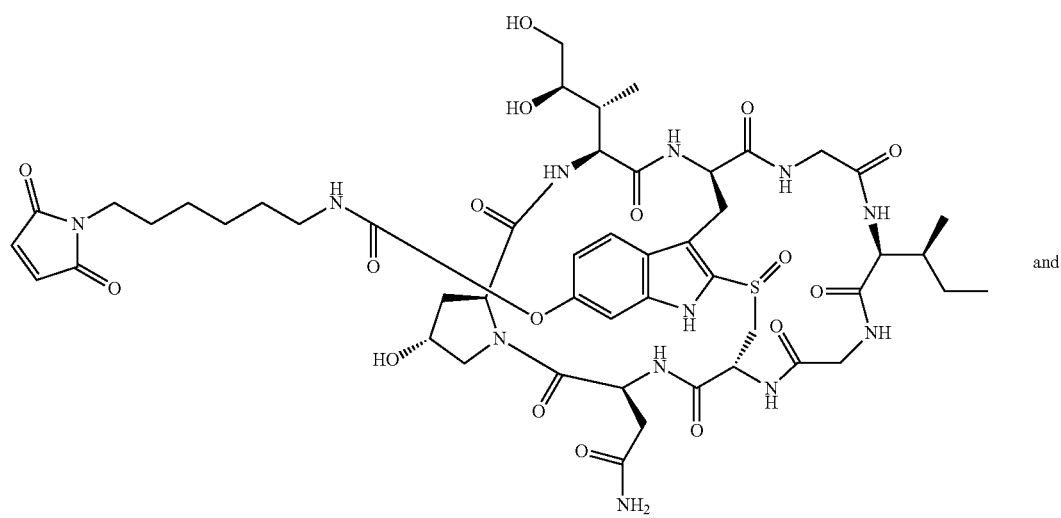 and
WO2014/043403

-continued

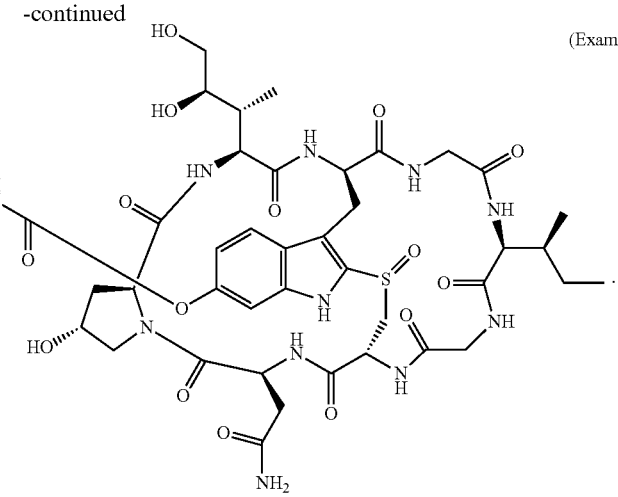

(Example 80)

The use of antibody-drug conjugates (ADCs) for the local delivery of cytotoxic or cytostatic agents, including drugs that kill or inhibit tumor cells, allows targeted delivery of the drug moiety to tumors, and intracellular accumulation therein. Syrigos and Epenetos (1999) *Anticancer Res.* 19:605-614; Niculescu-Duvaz and Springer (1997) *Adv. Drug Delivery Rev.* 26:151-172; U.S. Pat. No. 4,975,278; Baldwin et al. (1986) *Lancet* (Mar. 15, 1986):603-05; Thorpe (1985) "Antibody Carriers of Cytotoxic Agents in Cancer Therapy: A Review," in Monoclonal Antibodies '84: Biological and Clinical Applications, A. Pinchera et al. (eds.), pp. 475-506. This type of delivery mechanism helps to minimize toxicity to normal cells that may occur from systemic administration of unconjugated drug agents. The toxins may cause their cytotoxic and cytostatic effects through a variety of mechanisms including tubulin binding, DNA binding, or topoisomerase inhibition. Both polyclonal antibodies and monoclonal antibodies have been reported as useful in these strategies. Rowland et al. (1986) *Cancer Immunol. Immunother.* 21:183-87. Toxins used in antibody-toxin conjugates include radioisotopes, bacterial toxins such as diphtheria toxin, plant toxins such as ricin, fungal toxins such as amatoxins (WO2010/115629, WO2012/041504 or WO2012/119787), and small molecule toxins such as geldanamycin (Mandler et al. (2000) *J. Natl. Cancer Inst.* 92(19):1573-1581; Mandler et al. (2000) *Bioorg. Med. Chem. Lett.* 10:1025-1028; Mandler et al. (2002) *Bioconjugate Chem.* 13:786-791), maytansinoids (EP 1391213; Liu et al. (1996) *Proc. Natl. Acad. Sci. USA* 93:8618-8623), calicheamicin (Lode et al. (1998) *Cancer Res.* 58:2928; Hinman et al. (1993) *Cancer Res.* 53:3336-3342), daunomycin, doxorubicin, methotrexate, and vindesine (Rowland et al. (1986), supra).

Several antibody-drug conjugates have shown promising results against cancer in clinical trials, including ZEVALIN® (ibritumomab tiuxetan, Biogen/Idec), an antibody-radioisotope conjugate composed of a murine IgG1 kappa monoclonal antibody (directed against the CD20 antigen found on the surface of normal and malignant B lymphocytes) connected with an 111In or 90Y radioisotope via a thiourea linker-chelator.

The use of antibody-drug conjugates (ADCs) for the local delivery of cytotoxic or cytostatic agents, including drugs that kill or inhibit tumor cells, allows targeted delivery of the drug moiety to tumors, and intracellular accumulation therein. This type of delivery mechanism helps to minimize toxicity to normal cells that may occur from systemic administration of unconjugated drug agents. The toxins may cause their cytotoxic and cytostatic effects through a variety of mechanisms including tubulin binding.

As such, there remains a need for potent RNA polymerase inhibitor antibody conjugates with desirable pharmaceutical properties.

SUMMARY

The present disclosure provides improved amatoxin derivatives used in an ADC (antibody drug conjugate) structure. More specifically, the present disclosure provides an antibody drug conjugate (ADC) having the structure of Formula I

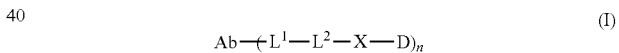

or a pharmaceutically acceptable salt thereof,
wherein:
Ab is a monoclonal antibody;
$L^1$-$L^2$ is a linker selected from the group consisting of

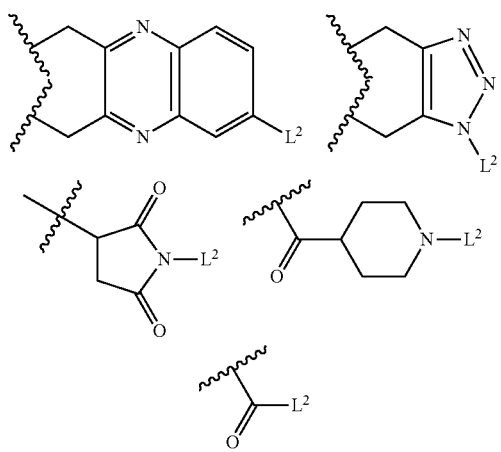

whereby the wavy line indicates the point of attachment to Ab;

$L^2$-X is a linker having structure of

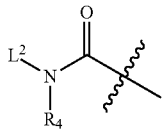

wherein $R_4$ is hydrogen, $C_{1-6}$ alkyl, —$(CH_2CH_2O)_m$—, or the combination thereof, and m is an integer from 1-24;

wherein the wavy line indicates the point of attachment to D

D is a drug moiety active agent derived from amatoxin and selected from the group consisting of alpha-amanitin, beta-amanitin, gamma-amanitin, and epsilon-amanitin having the structure below:

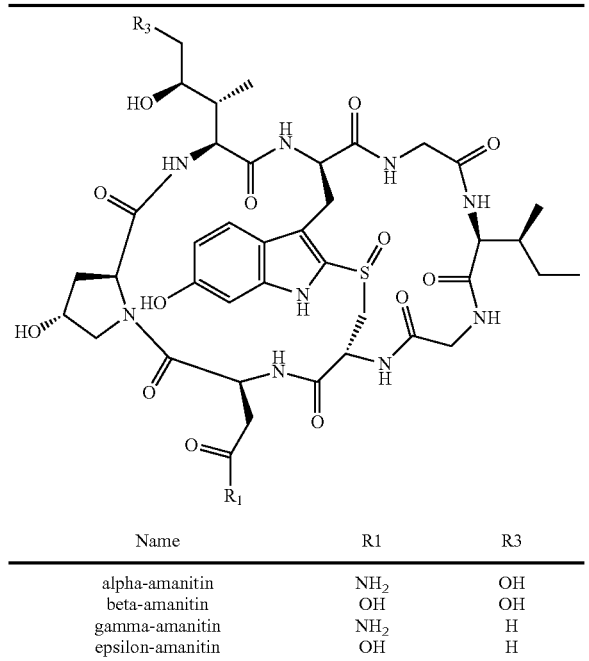

| Name | R1 | R3 |
|---|---|---|
| alpha-amanitin | NH$_2$ | OH |
| beta-amanitin | OH | OH |
| gamma-amanitin | NH$_2$ | H |
| epsilon-amanitin | OH | H | n is an integer from 1-10;

$L^2$ is a linker selected from the group consisting of an amino acid, peptide consisting of up to 10 amino acids, —$(CH_2)_p$—, —$(CH_2CH_2O)_m$—, —C(O)NH—, —NHC(O)—, PAB (p-aminobenzyl), Val-Cit-PAB, Val-Ala-PAB, Ala-Ala-Asn-PAB, —$R_6OC(O)NR_5$—, —$R_8$—S—S—$R_7$, and combinations thereof, wherein $R_5$ is selected from the group consisting of hydrogen, $C_{1-6}$ alkyl, —$(CH_2)_p$—, —$(CH_2CH_2O)_m$—, and combinations thereof;

$R_6$ is selected from the group consisting of an amino acid, peptide consisting of up to 10 aminoacids, $C_{1-6}$ alkyl, —$(CH_2)_p$—, —$(CH_2CH_2O)_m$—, —C(O)NH—, —NHC(O)—, PAB, Val-Cit-PAB, Val-Ala-PAB, Ala-Ala-Asn-PAB and combinations thereof;

$R_7$ is $C_{2-6}$ alkylene, or —$(CH_2CH_2O)_m$—;

$R_8$ is selected from the group consisting of an amino acid, peptide consisting of up to 10 aminoacids, $C_{1-6}$ alkyl, $C_{1-6}$ alkylene, substituted $C_{1-6}$ alkylene, —C(O)NH—, —C(O)—NH—CHR$_9$—CR$_{10}$R$_{11}$—, —NHC(O)—CHR$_9$—CR$_{10}$R$_{11}$—, —$(CH_2CH_2O)_m$—, PAB, Val-Cit-PAB, Val-Ala-PAB, Ala-Ala-Asn-PAB, and combinations thereof;

wherein $R_9$ is selected from the group consisting of hydrogen, $C_{1-6}$ alkyl, $C_{1-6}$ alkylene, —$(CH_2CH_2O)_m$—, —C(O)NH—, —NHC(O)—, —C(O)NH—$(CH_2)_p$—SO$_3$H, C(O)NH—$(CH_2)_p$—CO$_2$H, —NHC(O)—$(CH_2)_p$—SO$_3$H, —NHC(O)—$(CH_2)_p$—CO$_2$H and combinations thereof;

$R_{10}$ and $R_{11}$ are each independently selected from the group consisting of hydrogen, $C_{1-6}$ alkyl, and combinations thereof;

wherein —$R_6OC(O)NR_5$— is connected to $L^1$ through $R_5$ or $R_6$;

wherein —$R_8$—S—S—$R_7$— is connected to $L^1$ through $R_8$;

m is an integer from 1-24; and p is an integer from 1-6.

In another aspect, $L^2$ in the compounds having the structure of Formula I is a linker selected from the group consisting of an amino acid, peptide consisting of up to 10 amino acids, —$(CH_2)_p$—, —$(CH_2CH_2O)_m$—, —C(O)NH—, —NHC(O)—, PAB (p-aminobenzyl), -Val-Cit-PAB-, -Val-Ala-PAB-, -Ala-Ala-Asn-PAB-, —$R_6OC(O)NR_8$—, —$R_8$—S—S—$R_7$, and combinations thereof, wherein $R_5$ is selected from the group consisting of hydrogen, $C_{1-6}$ alkyl, —$(CH_2)_p$—, —$(CH_2CH_2O)_m$—, and combinations thereof;

$R_6$ is selected from the group consisting of an amino acid, peptide consisting of up to 10 aminoacids, $C_{1-6}$ alkyl, —$(CH_2)_p$—, —$(CH_2CH_2O)_m$—, —C(O)NH—, —NHC(O)—, PAB, -Val-Cit-PAB-, -Val-Ala-PAB-, -Ala-Ala-Asn-PAB- and combinations thereof;

$R_7$ is $C_{2-6}$ alkylene, or —$(CH_2CH_2O)_m$—;

$R_8$ is selected from the group consisting of an amino acid, peptide consisting of up to 10 aminoacids, $C_{1-6}$ alkyl, $C_{1-6}$ alkylene, substituted $C_{1-6}$ alkylene, —C(O)NH—, —C(O)—NH—CHR$_9$—CR$_{10}$R$_{11}$—, —NHC(O)—CHR$_9$—CR$_{10}$R$_{11}$—, —$(CH_2CH_2O)_m$—, PAB, -Val-Cit-PAB-, -Val-Ala-PAB-, -Ala-Ala-Asn-PAB-, and combinations thereof;

wherein $R_9$ is selected from the group consisting of hydrogen, $C_{1-6}$ alkyl, $C_{1-6}$ alkylene, —$(CH_2CH_2O)_m$—, —C(O)NH—, —NHC(O)—, —C(O)NH—$(CH_2)_p$—SO$_3$H, C(O)NH—$(CH_2)_p$—CO$_2$H, —NHC(O)—$(CH_2)_p$—SO$_3$H, —NHC(O)—$(CH_2)_p$—CO$_2$H and combinations thereof;

$R_{10}$ and $R_{11}$ are each independently selected from the group consisting of hydrogen, $C_{1-6}$ alkyl, and combinations thereof;

wherein —$R_6OC(O)NR_5$— is connected to $L^1$ through $R_5$ or $R_6$;

wherein —$R_8$—S—S—$R_7$— is connected to $L^1$ through $R_8$;

m is an integer from 1-24; and p is an integer from 1-6, wherein the remaining values are as described above for Formula I.

In yet another aspect, $L^2$ in the compounds having the structure of Formula I is a linker selected from the group consisting of an amino acid, peptide consisting of up to 10 amino acids, —$(CH_2)_p$—, —$(CH_2CH_2O)_m$—, —C(O)NH—, —NH(4-phenyl)CH$_2$O—, -Val-Cit-NH(4-phenyl)CH$_2$O—, -Val-Ala-NH(4-phenyl)CH$_2$O—, -Ala-Ala-Asn-NH(4-phenyl)CH$_2$O—, —$R_6OC(O)NR_8$—, —$R_8$—S—S—$R_7$—, and combinations thereof, wherein $R_5$ is selected from the group consisting of hydrogen, $C_{1-6}$ alkyl, —$(CH_2)_p$—, —$(CH_2CH_2O)_m$—, and combinations thereof;

$R_6$ is selected from the group consisting of an amino acid, peptide consisting of up to 10 amino acids, $C_{1-6}$ alkyl, —$(CH_2)_p$—, —$(CH_2CH_2O)_m$—, —C(O)NH—, —NH(4- phenyl)CH$_2$—, -Val-Cit-NH(4-phenyl)CH$_2$—, -Val-Ala-NH(4-phenyl)CH$_2$—, -Ala-Ala-Asn-NH(4-phenyl)CH$_2$—, and combinations thereof;

R$_7$ is C$_{2-6}$ alkylene, or —(CH$_2$CH$_2$O)$_m$—;

R$_8$ is selected from the group consisting of an amino acid, peptide consisting of up to 10 amino acids, C$_{1-6}$ alkyl, C$_{1-6}$ alkylene, substituted C$_{1-6}$ alkylene, —C(O)—NH—CHR$_9$—CR$_{10}$R$_{11}$—, —NHC(O)—CHR$_9$—CR$_{10}$R$_{11}$—, —(CH$_2$CH$_2$O)$_m$—, -PAB-, -Val-Cit-NH(4-phenyl)CH$_2$—, -Val-Ala-NH(4-phenyl)CH$_2$—, -Ala-Ala-Asn-NH(4-phenyl)CH$_2$—, and combinations thereof;

wherein R$_9$ is selected from the group consisting of hydrogen, C$_{1-6}$ alkyl, C$_{1-6}$ alkylene, —(CH$_2$CH$_2$O)$_m$—, —C(O)NH—, —NHC(O)—, —C(O)NH—(CH$_2$)$_p$—SO$_3$H, —C(O)NH—(CH$_2$)$_p$—CO$_2$H, —NHC(O)—(CH$_2$)$_p$—SO$_3$H, —NHC(O)—(CH$_2$)$_p$—CO$_2$H and combinations thereof;

R$_{10}$ and R$_{11}$ are each independently selected from the group consisting of hydrogen, C$_{1-6}$ alkyl, and combinations thereof;

wherein —R$_6$OC(O)NR$_5$— is connected to L$^1$ through R$_6$;

wherein —R$_8$—S—S—R$_7$— is connected to L$^1$ through R$_8$;

m is an integer from 1-24; and p is an integer from 1-6, wherein the remaining values are as described above for Formula I.

Preferably, D has a structure of Formula II:

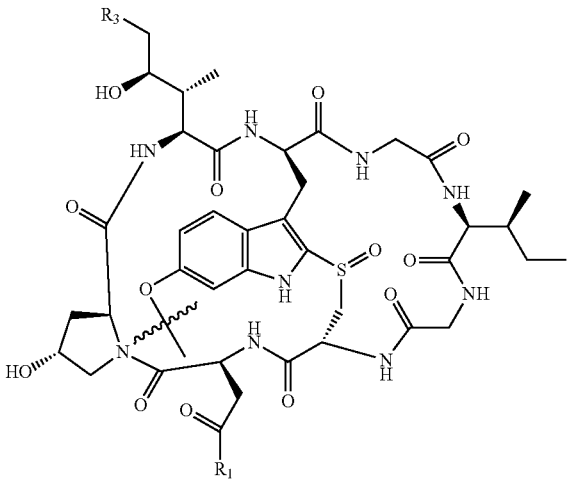

(II)

whereby the wavy line indicates the point of attachment to X;

wherein R$_1$ is NH$_2$ or OR$_2$, wherein R$_2$ is H, or C$_1$-C$_{10}$ alkyl, and wherein R$_3$ is H or OH.

Preferably, the disclosed ADC is selected from the group consisting of:

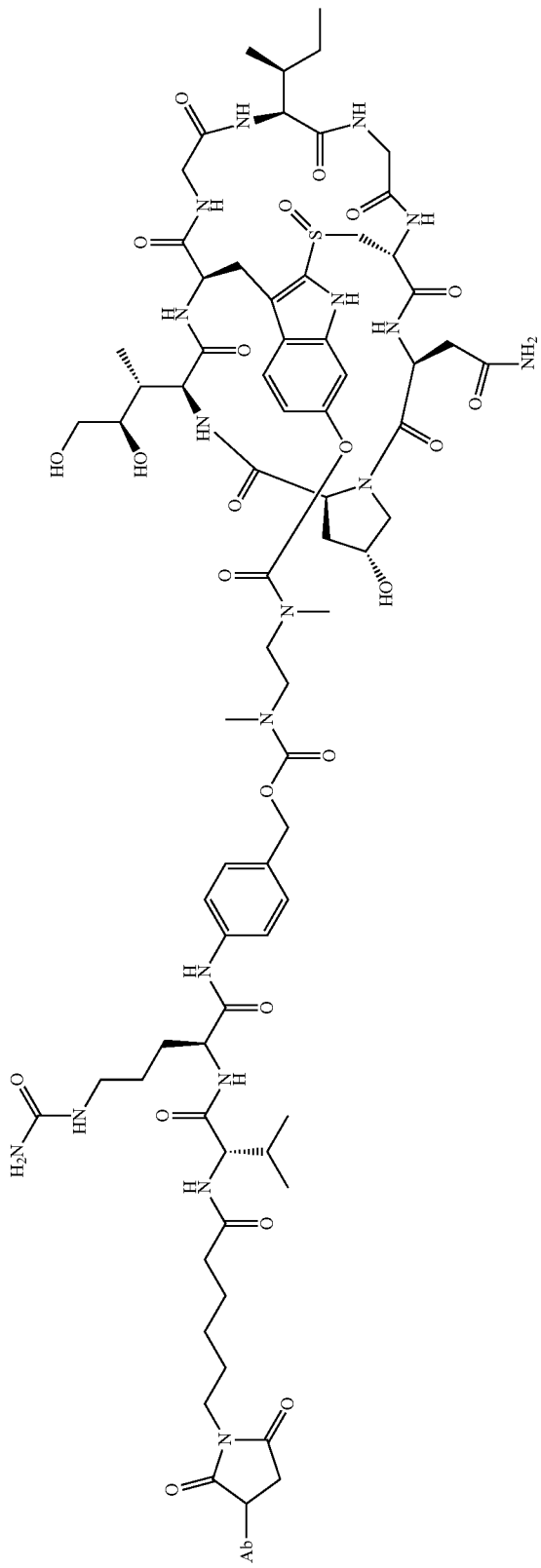

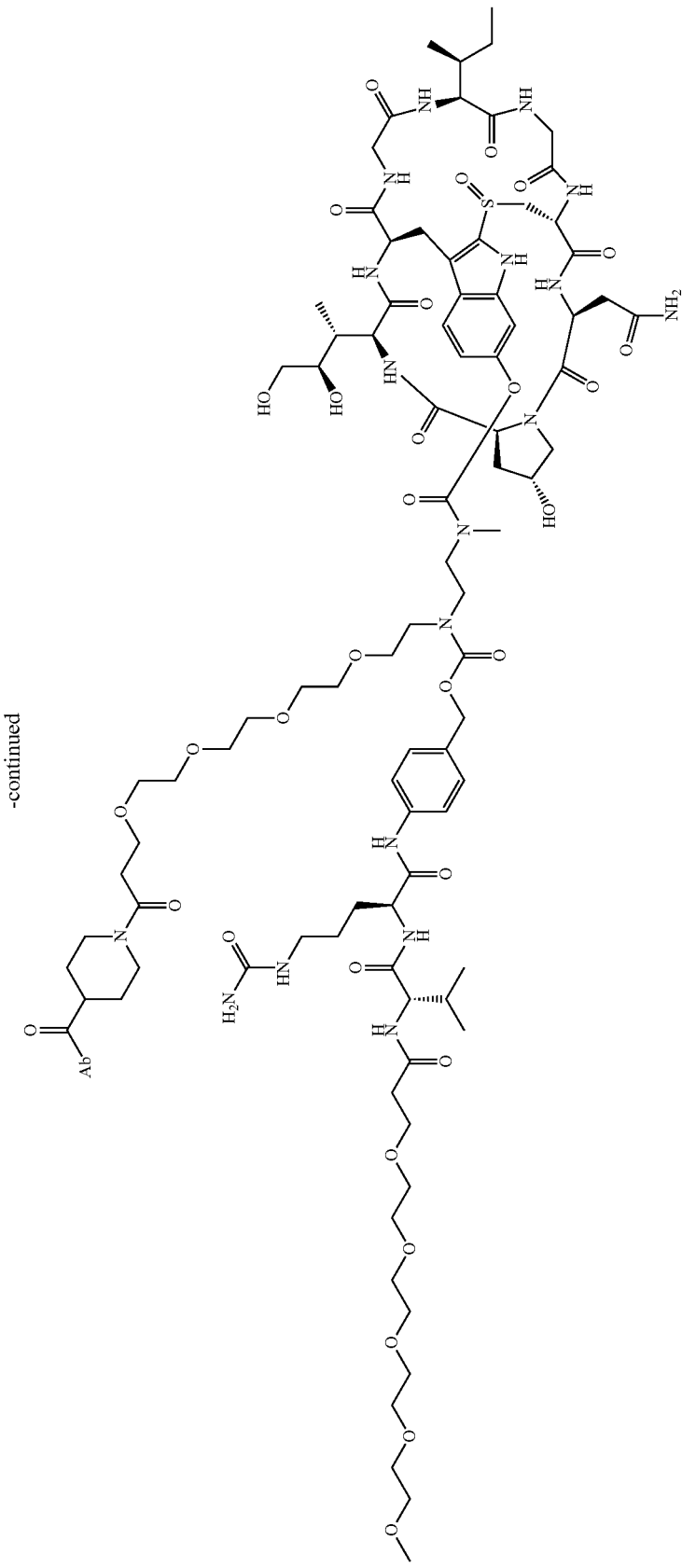
-continued

-continued
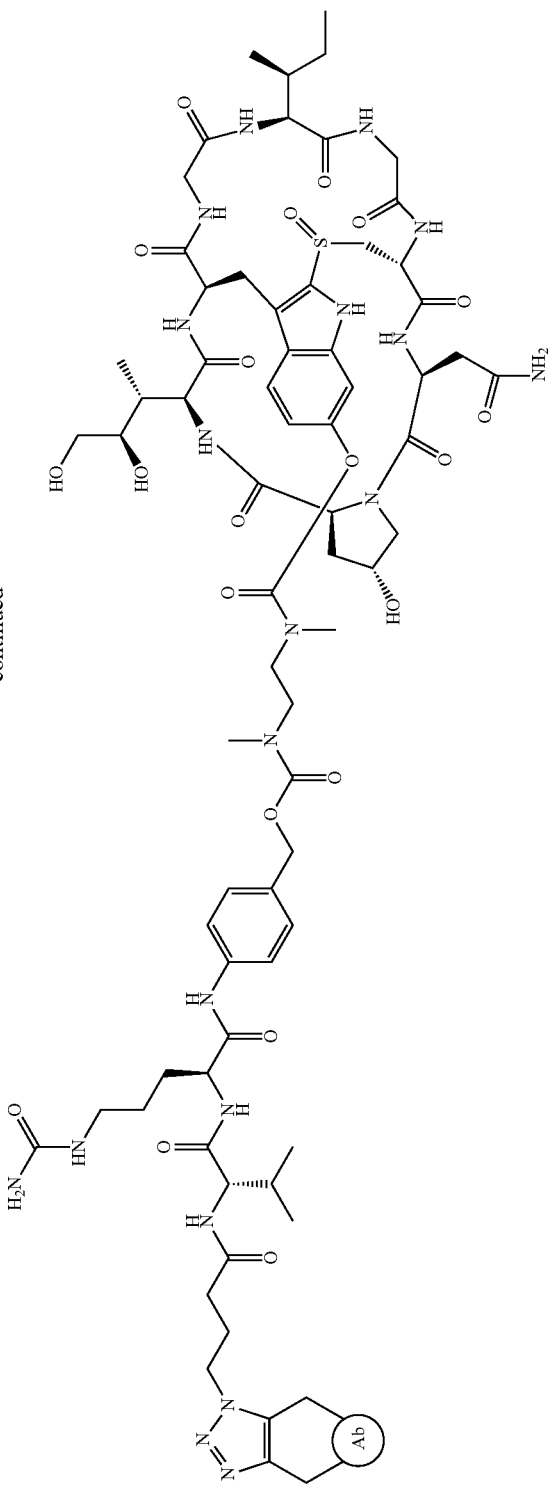

-continued
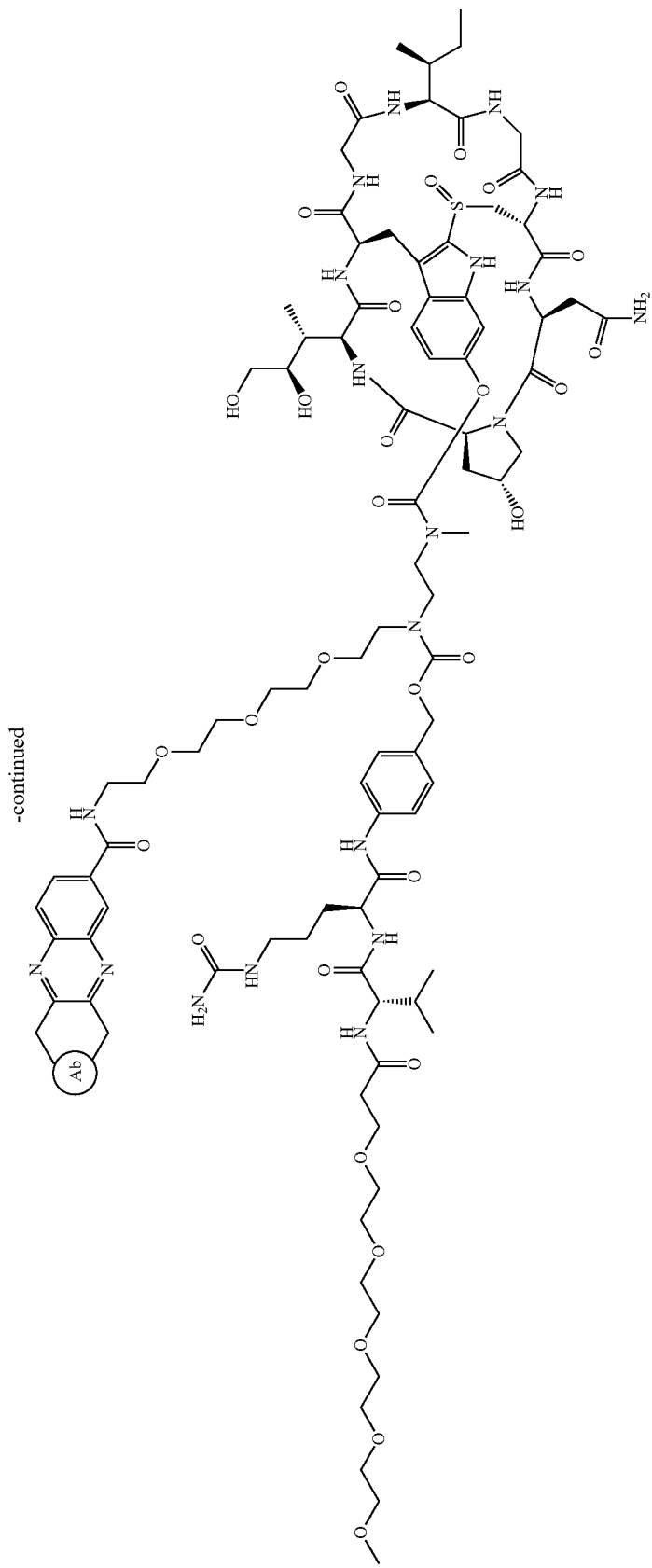

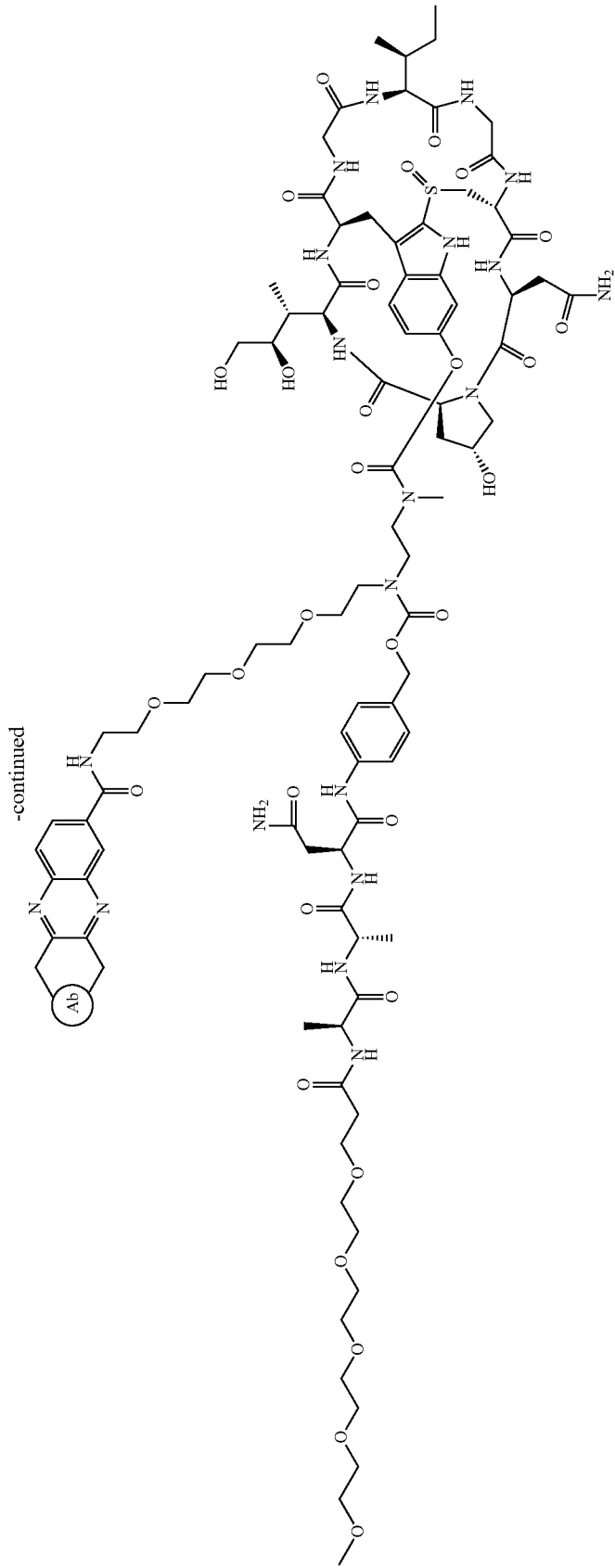

21
-continued
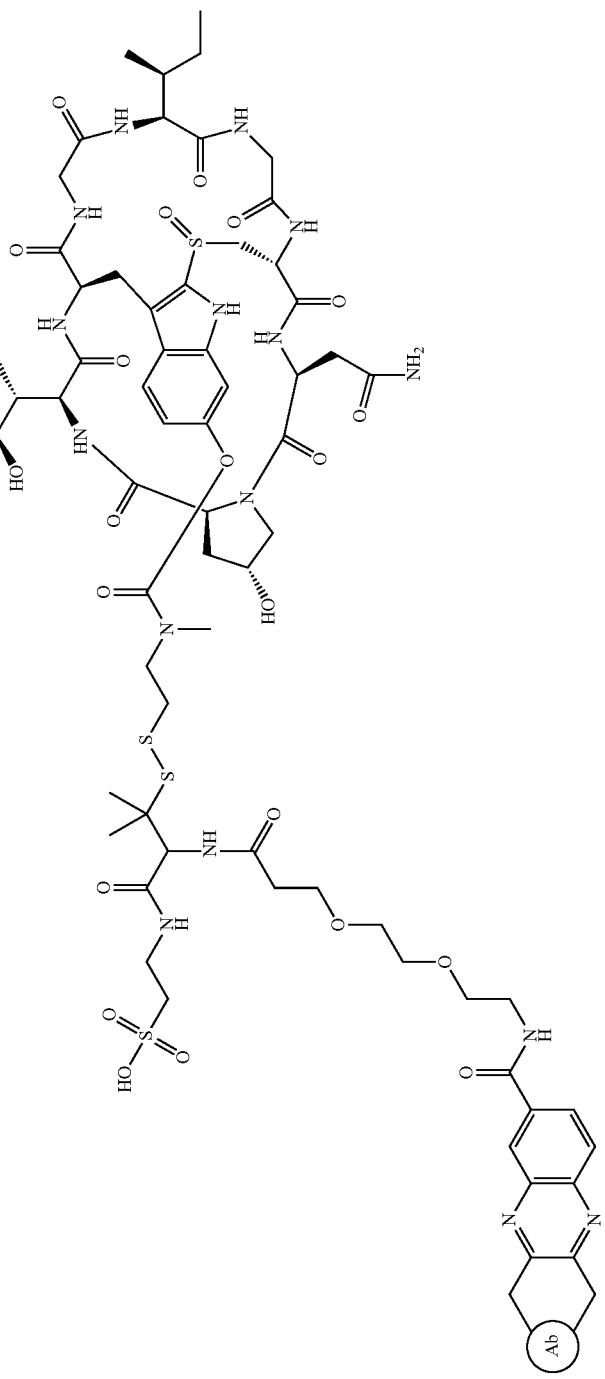
22
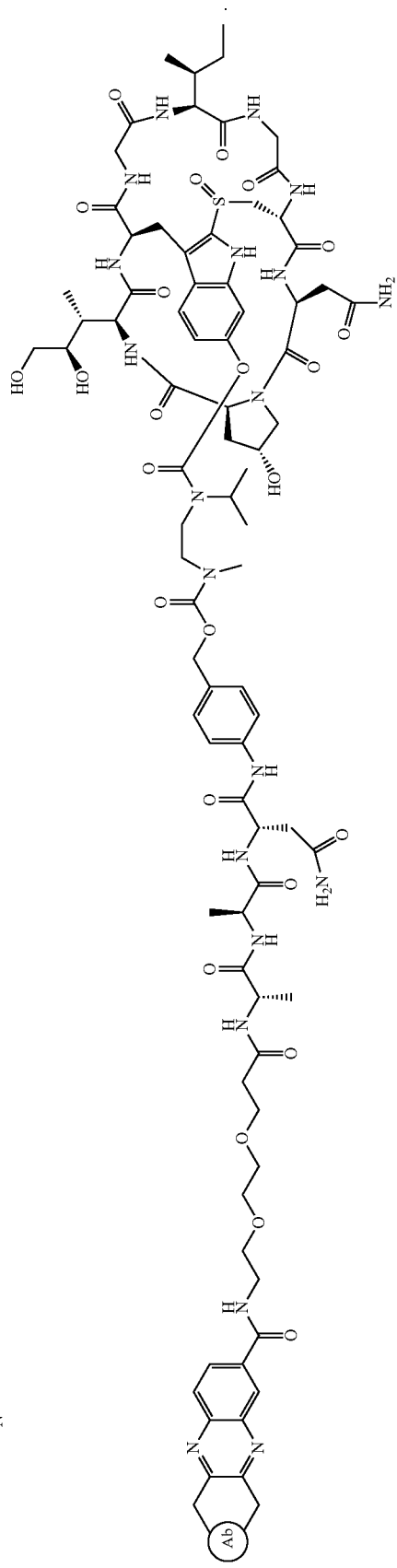

DETAILED DESCRIPTION

TABLE 1

Figure 1:
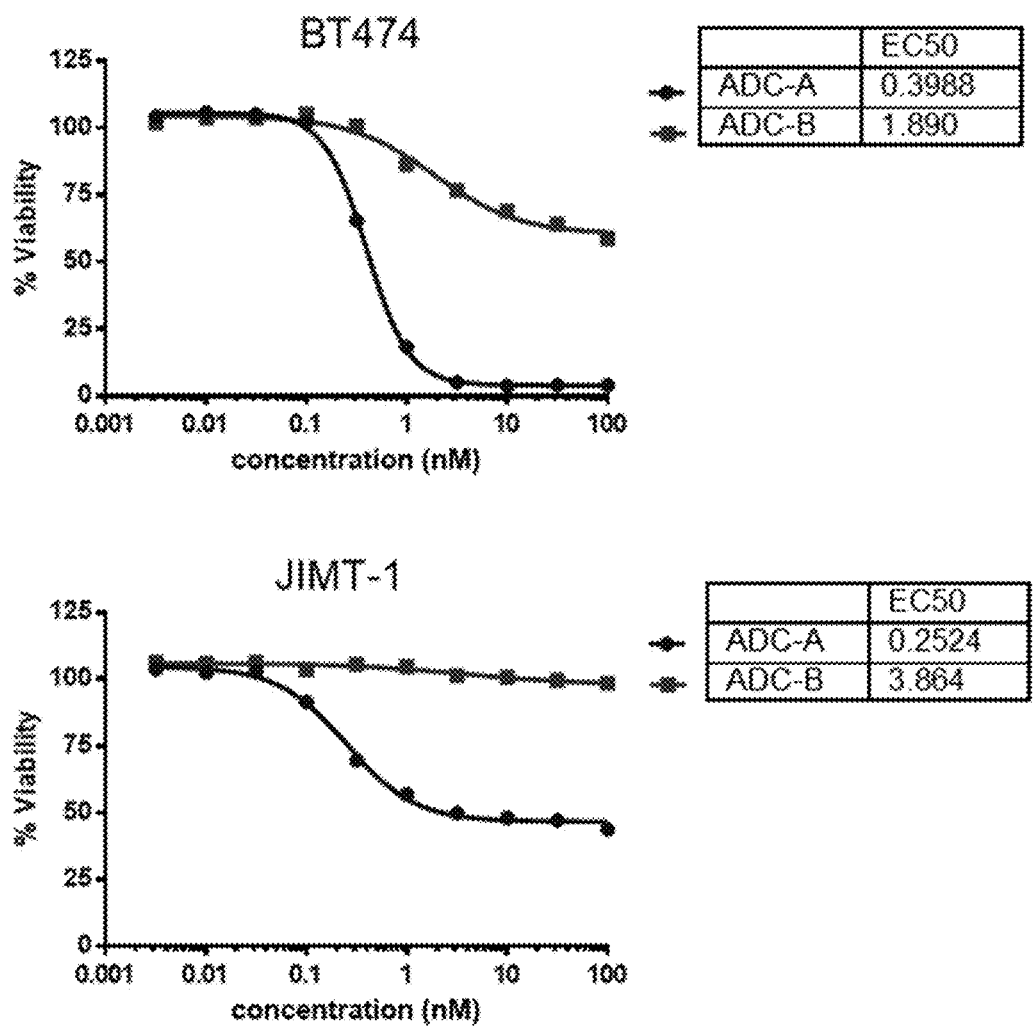
FIG. 1 shows a comparison of in vitro cytotoxicity of ADC A (22) and ADC B on four cell lines, one cell line in each of the four panels of FIG. 1.

Examples of compounds synthesized ("Ab" stands for antibody).

| Compound # | Structure |
|---|---|
| 6 | 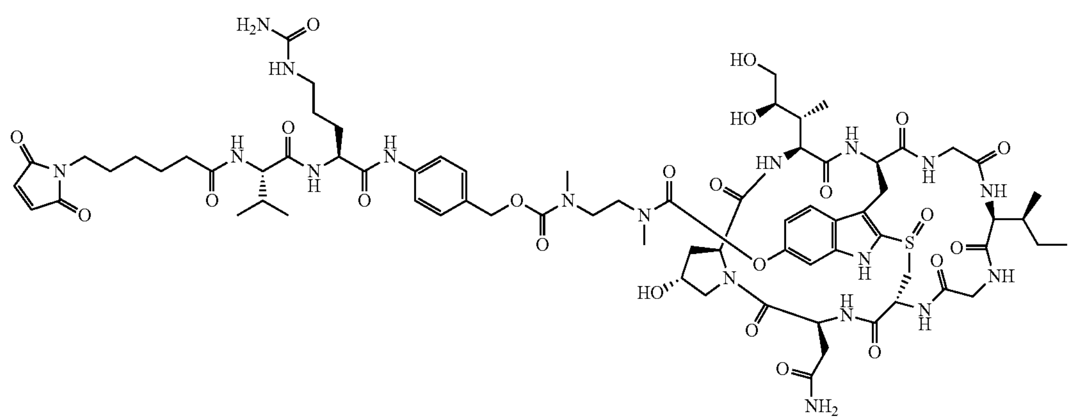 [SMILES: CC[C@H](C)[C@@H]1NC(=O)CNC(=O)[C@H]2Cc3c([nH]c4cc(OC(=O)N(C)CCN(C)C(=O)OCc5ccc(NC(=O)[C@H](CCCNC(N)=O)NC(=O)[C@@H](NC(=O)CCCCCN6C(=O)C=CC6=O)C(C)C)cc5)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2] |
| 8 | 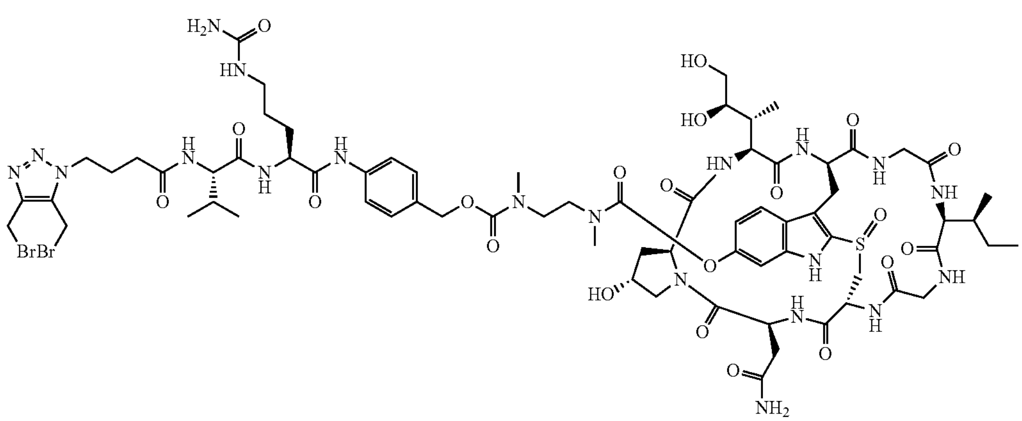 [SMILES: CC[C@H](C)[C@@H]1NC(=O)CNC(=O)[C@H]2Cc3c([nH]c4cc(OC(=O)N(C)CCN(C)C(=O)OCc5ccc(NC(=O)[C@H](CCCNC(N)=O)NC(=O)[C@@H](NC(=O)CCCn6nnc(CBr)c6CBr)C(C)C)cc5)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2] |

TABLE 1-continued

Examples of compounds synthesized ("Ab" stands for antibody).

| Compound # | Structure |
|---|---|
| 10 | 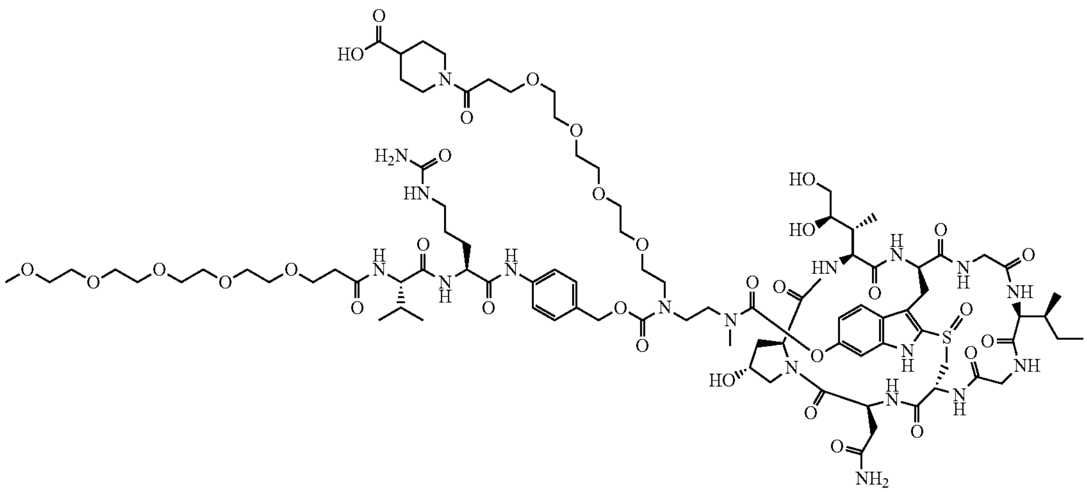 [SMILES: CC[C@H](C)[C@@H]1NC(=O)CNC(=O)[C@H]2Cc3c([nH]c4cc(OC(=O)N(C)CCN(CCOCCOCCOCCOCCC(=O)N5CCC(C(=O)O)CC5)C(=O)OCc5ccc(NC(=O)[C@H](CCCNC(N)=O)NC(=O)[C@@H](NC(=O)CCOCCOCCOCCOCCOC)C(C)C)cc5)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2] |
| 14 | 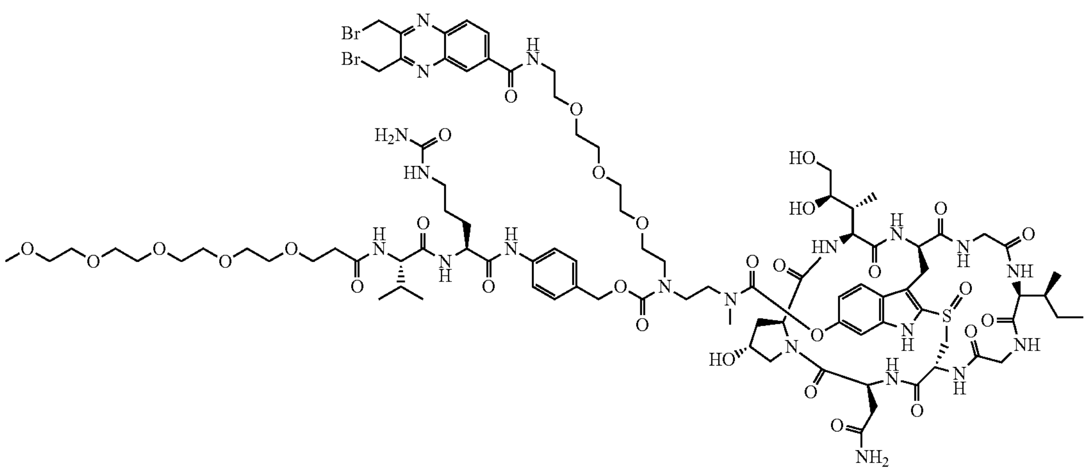 [SMILES: CC[C@H](C)[C@@H]1NC(=O)CNC(=O)[C@H]2Cc3c([nH]c4cc(OC(=O)N(C)CCN(CCOCCOCCOCCNC(=O)c5ccc6nc(CBr)c(CBr)nc6c5)C(=O)OCc5ccc(NC(=O)[C@H](CCCNC(N)=O)NC(=O)[C@@H](NC(=O)CCOCCOCCOCCOCCOC)C(C)C)cc5)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2] |
| 17 | 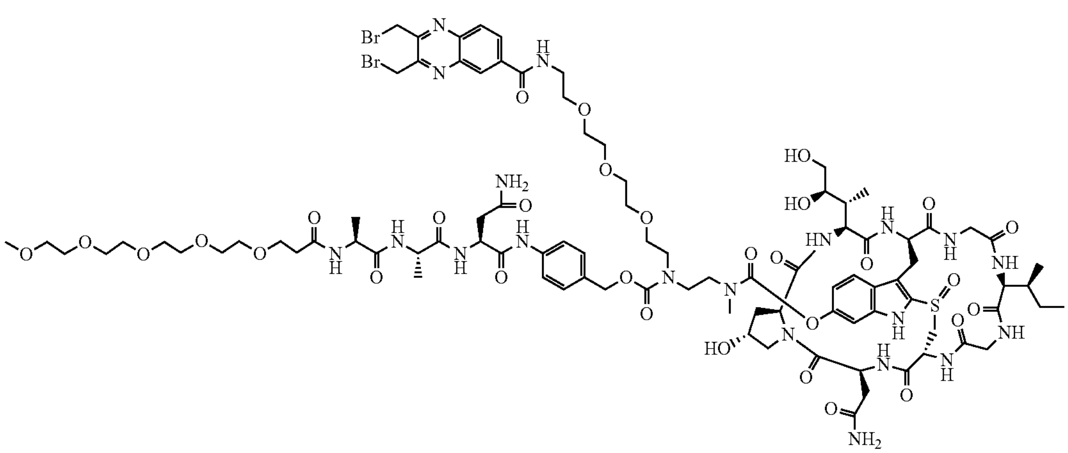 [SMILES: CC[C@H](C)[C@@H]1NC(=O)CNC(=O)[C@H]2Cc3c([nH]c4cc(OC(=O)N(C)CCN(CCOCCOCCOCCNC(=O)c5ccc6nc(CBr)c(CBr)nc6c5)C(=O)OCc5ccc(NC(=O)[C@H](CC(N)=O)NC(=O)[C@H](C)NC(=O)[C@H](C)NC(=O)CCOCCOCCOCCOCCOC)cc5)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2] |

TABLE 1-continued

Examples of compounds synthesized ("Ab" stands for antibody).

| Compound # | Structure |
| --- | --- |
| 21 | 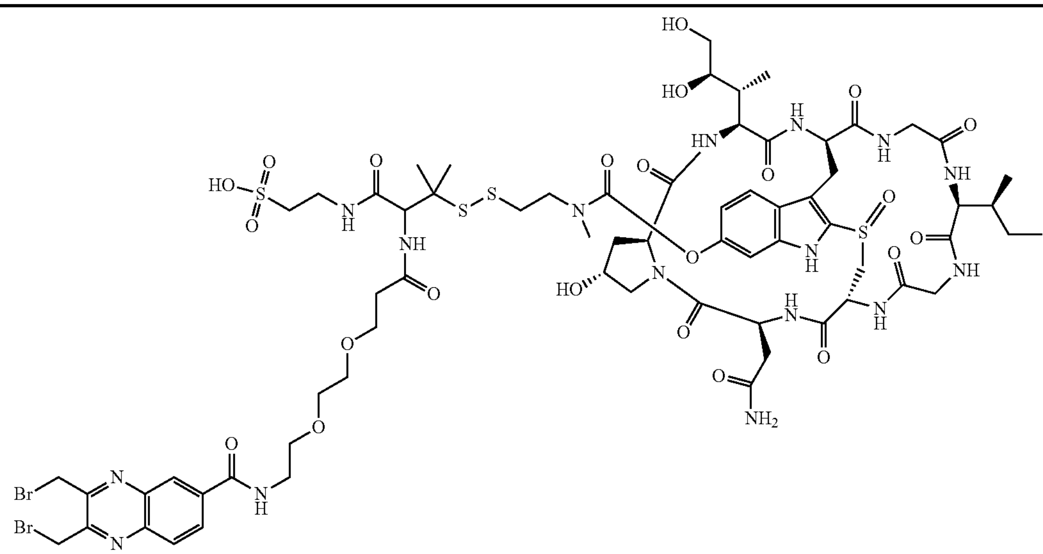 |
| 28 | 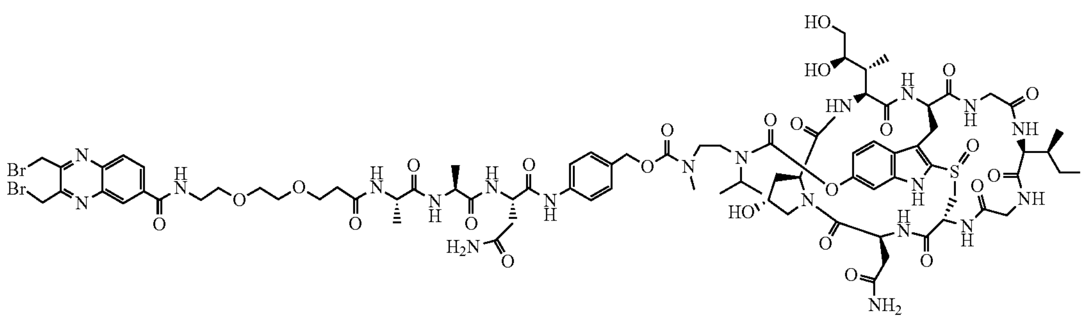 [SMILES: CC[C@H](C)[C@@H]1NC(=O)CNC(=O)[C@H]2Cc3c([nH]c4cc(OC(=O)N(CCN(C)C(=O)OCc5ccc(NC(=O)[C@H](CC(N)=O)NC(=O)[C@H](C)NC(=O)[C@H](C)NC(=O)CCOCCOCCNC(=O)c6ccc7nc(CBr)c(CBr)nc7c6)cc5)C(C)C)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2] |

TABLE 2

Examples of antibody drug conjugates of Formula I

| Compound # | Structure |
| --- | --- |
| 22 | 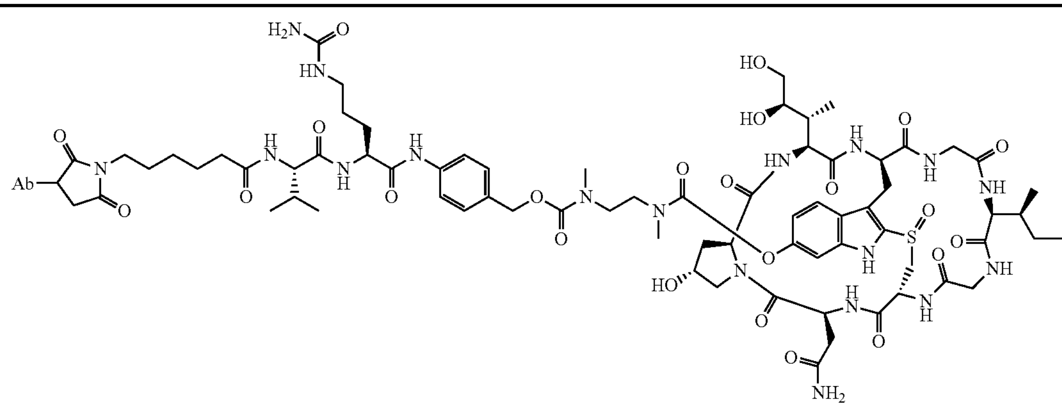 |

TABLE 2-continued
Examples of antibody drug conjugates of Formula I
| Compound # | Structure |
|---|---|
| 23 | 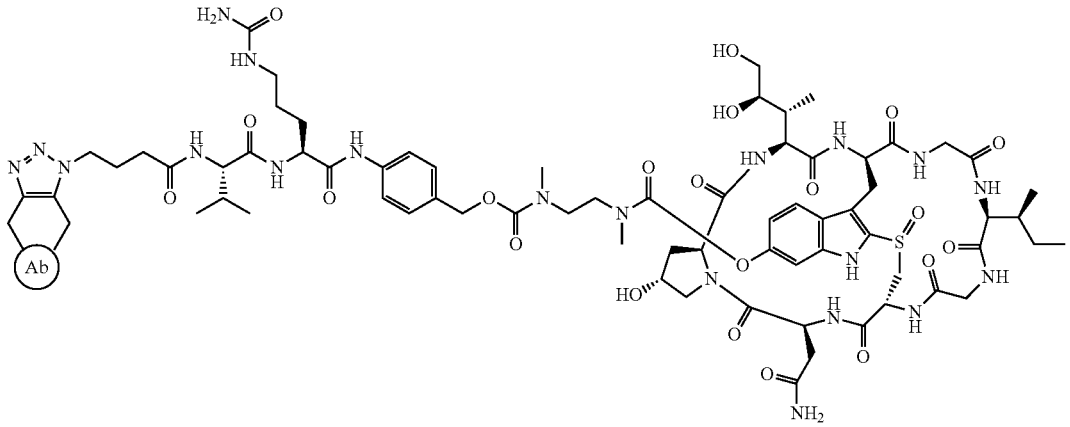 [SMILES: CCc1nnn(CCCC(=O)N[C@H](C(=O)N[C@@H](CCCNC(N)=O)C(=O)Nc2ccc(COC(=O)N(C)CCN(C)C(=O)Oc3ccc4c5c([nH]c4c3)S(=O)C[C@@H]3NC(=O)CNC(=O)[C@H]([C@@H](C)CC)NC(=O)CNC(=O)[C@@H](C5)NC(=O)[C@H]([C@@H](C)[C@@H](O)CO)NC(=O)[C@@H]4C[C@@H](O)CN4C(=O)[C@H](CC(N)=O)NC3=O)cc2)C(C)C)c1CC] |
| 24 | 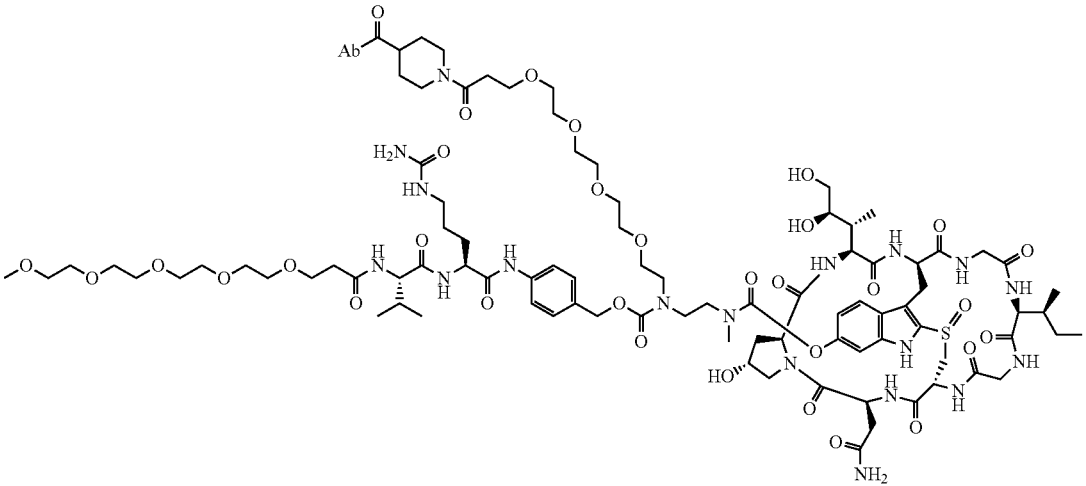 |
| 25 | 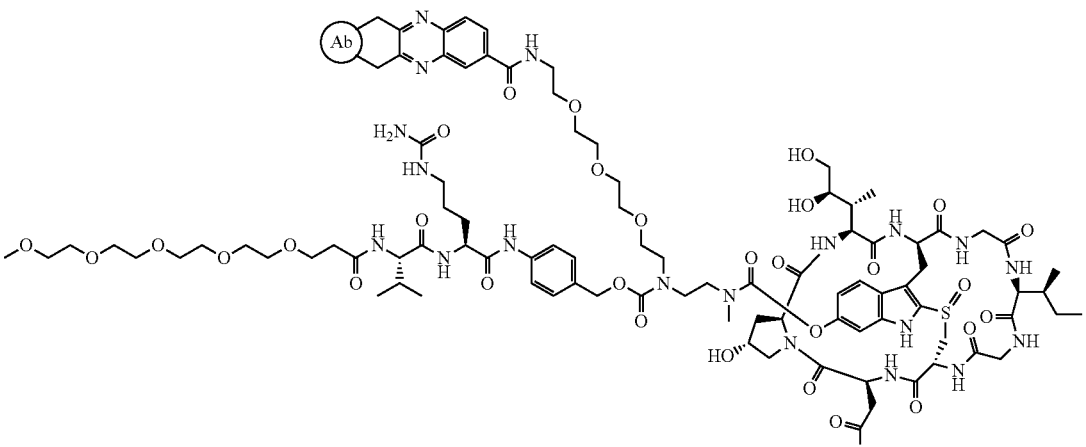 |

TABLE 2-continued
Examples of antibody drug conjugates of Formula I
| Compound # | Structure |
|---|---|
| 26 | 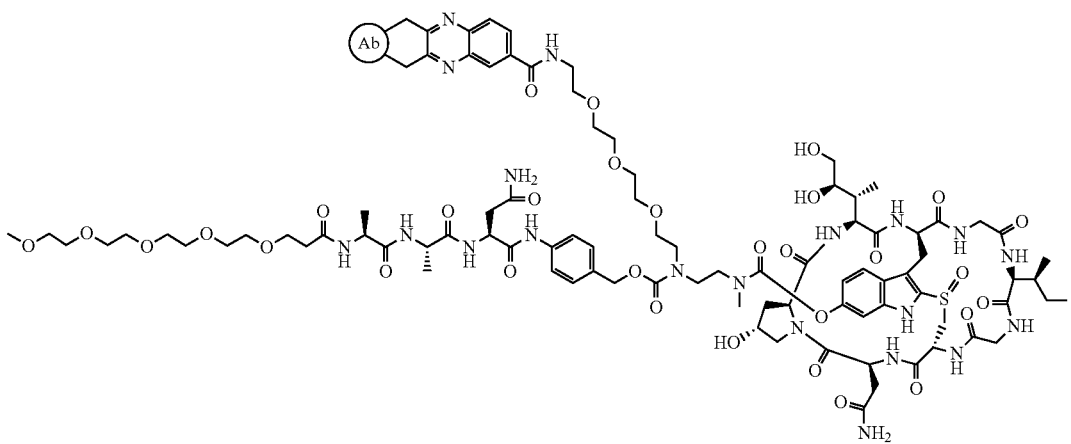 [SMILES: CCc1nc2ccc(C(=O)NCCOCCOCCOCCN(CCN(C)C(=O)Oc3ccc4c5c([nH]c4c3)S(=O)C[C@@H]3NC(=O)CNC(=O)[C@H]([C@@H](C)CC)NC(=O)CNC(=O)[C@@H](C5)NC(=O)[C@H]([C@@H](C)[C@@H](O)CO)NC(=O)[C@@H]4C[C@@H](O)CN4C(=O)[C@H](CC(N)=O)NC3=O)C(=O)OCc3ccc(NC(=O)[C@H](CC(N)=O)NC(=O)[C@H](C)NC(=O)[C@H](C)NC(=O)CCOCCOCCOCCOCCOC)cc3)cc2nc1CC] |
| 27 | 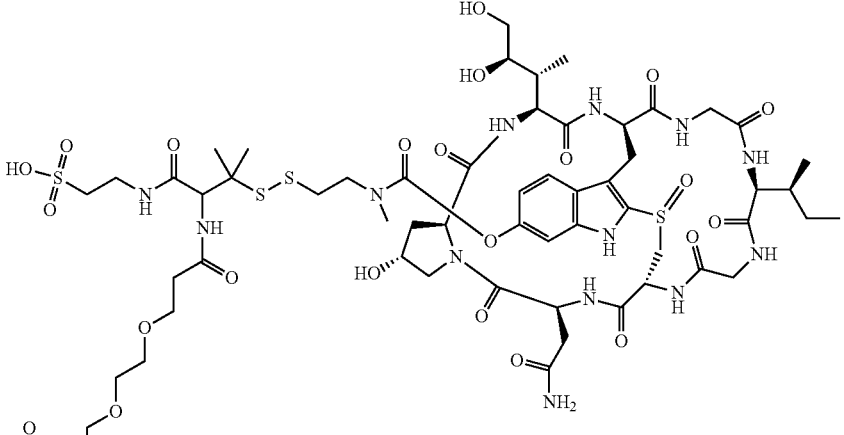 |
| 29 | 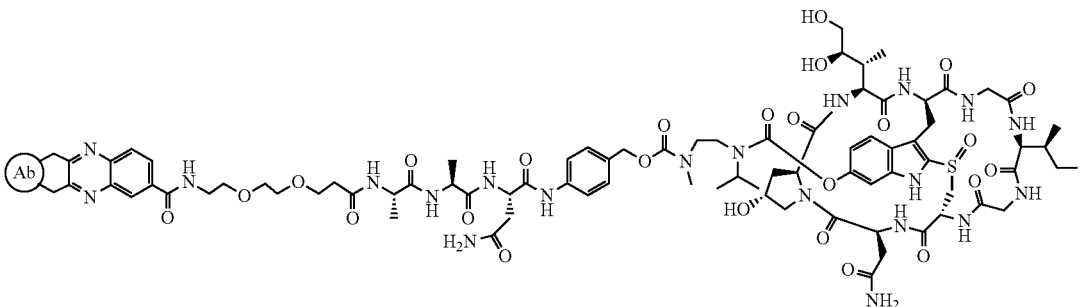 |

Definitions

As used herein, common organic abbreviations are defined as follows:
Ac Acetyl
aq. Aqueous
BOC or Boc tert-Butoxycarbonyl
Bu n-Butyl
° C. Temperature in degrees Centigrade
Cit Citrulline
DCM methylene chloride
DEPC Diethylcyanophosphonate
DIC diisopropylcarbodiimide
DIEA Diisopropylethylamine
DMA N,N-Dimethylacetamide
DMF N,N-Dimethylformamide
DMSO Dimethylsulfoxide
EDC 1-Ethyl-3-(3-dimethylaminopropyl)carbodiimide
Et Ethyl
EtOAc Ethyl acetate
Eq Equivalents
Fmoc 9-Fluorenylmethoxycarbonyl
g Gram(s)
h Hour (hours)
HATU 2-(1H-7-azabenzotriazol-1-yl)-1,1,3,3-tetramethyl uronium hexafluorophosphate
HOBT N-Hydroxybenzotriazole
HOSu N-Hydroxysuccinimide
HPLC High-performance liquid chromatography
LC/MS Liquid chromatography-mass spectrometry
Me Methyl
MeOH Methanol
MeCN Acetonitrile
mL Milliliter(s)
MS mass spectrometry
PAB p-aminobenzyl
RP-HPLC reverse phase HPLC
rt room temperature
t-Bu tert-Butyl
TEA Triethylamine
Tert, t tertiary
TFA Trifluoracetic acid
THF Tetrahydrofuran
TLC Thin-layer chromatography
µL Microliter(s)

Where used, a hyphen (-) designates the point to which a group is attached to the defined variable. A hyphen on the left side indicates connectivity to the left side structural component of formula (I) and hyphen on the right side indicates connectivity to the right side structural component of formula (I). For example, unless other specified when $L_2$ is defined as $—(CH_2CH_2O)_m—$, it means that the attachment to $L^1$ is at the $—CH_2$ carbon and the attachment to X is at the oxygen atom.

General Synthesis Procedure—Formation of an Activated Ester (e.g. NHS) from an Acid An acid was dissolved in DCM (methylene chloride) and DMF (N,N'dimethyl formamide) was added to aid dissolution if necessary. N-hydroxysuccinimide (1.5 eq) was added, followed by EDC.HCl (1-Ethyl-3-(3-dimethylaminopropyl) carbodiimide) (1.5 eq). The reaction mixture was stirred at room temperature for 1 h until most of the acid was consumed. The progress of the reaction was monitored by RP-HPLC. The mixture was then diluted with DCM and washed successively with citric acid (aq. 10%) and brine. The organic layer was dried and concentrated to dryness. The crude product was optionally purified by RP-HPLC or silica gel column chromatography.

Example 1

Preparation of Compound 6

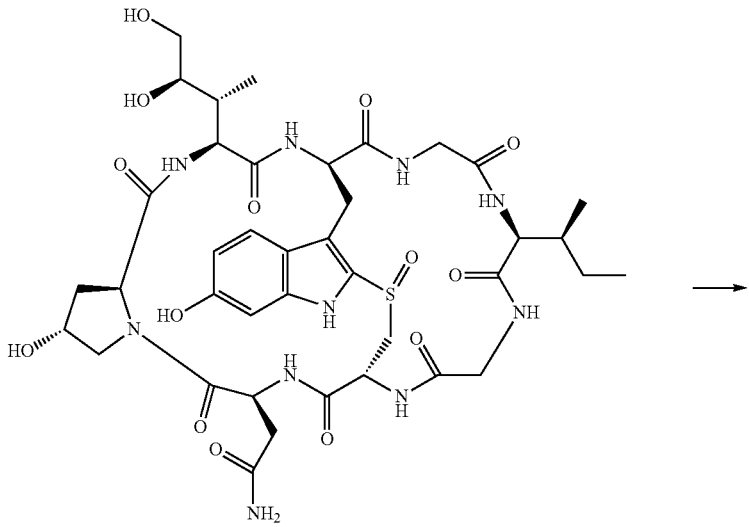

-continued
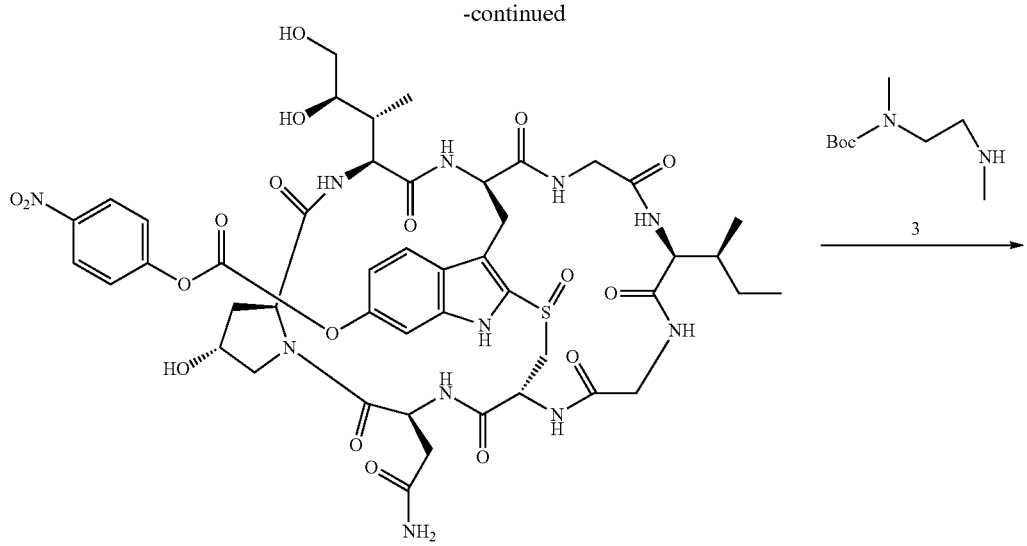
2
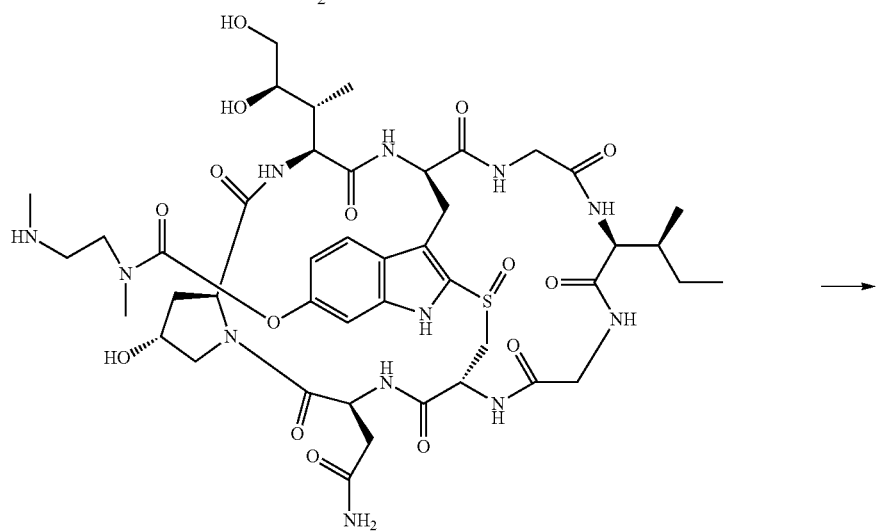
4
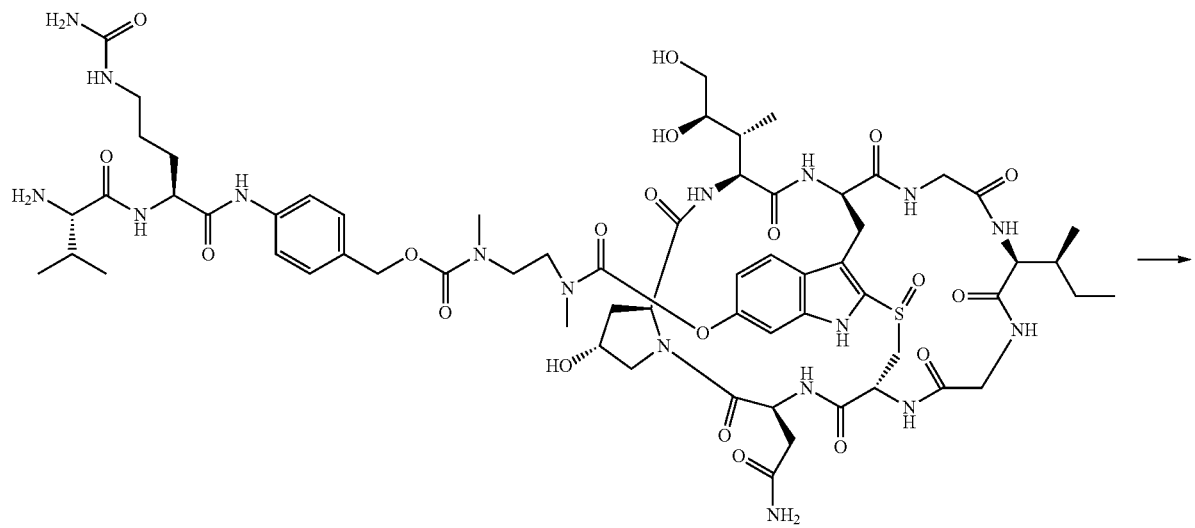
5

-continued

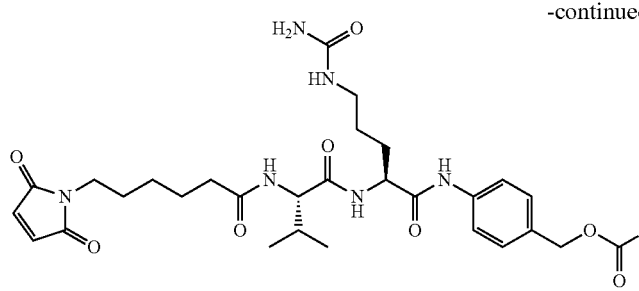

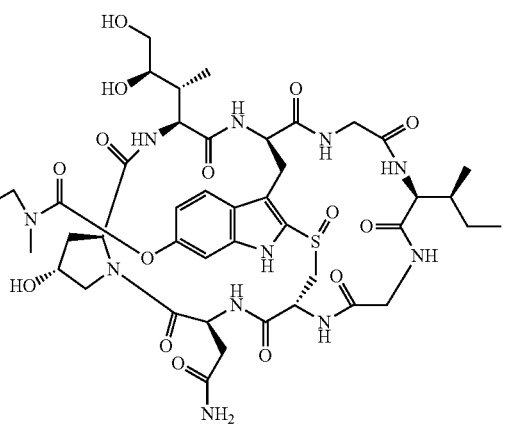

6

To a solution of alpha-amainitin 1 (46 mg, 50 µmol) in anhydrous dimethylsulfoxide (DMSO) (1 mL) was added bis (4-nitrophenol) carbonate (17 mg, 55 µmol), followed by diisopropylethylamine (DIEA, 10 µL). The mixture was stirred at room temperature for 30 minutes. Compound 3 (12 mg) was added, followed by DIEA (10 µL). LC/MS indicated all the compound 2 was consumed after 1 h. All the solvents were removed under reduced the pressure and the residue was treated with trifluoroacetic acid (TFA) in dichloromethane (DCM) (20%, v/v, 2 mL). The reaction mixture was concentrated after 30 min and the residue was purified by reverse phase HPLC to give compound 4 as a white solid in TFA salt form after lyophilization (45 mg, 78%). MS: m/z 1033.4 (M+H$^+$).

Compound 4 (45 mg) was dissolved in anhydrous dimethylformamide (DMF, 1 mL) and 9-Fluorenylmethyloxycarbonyl-valyl-citrullyl-(4-aminobenzyl)-(4-nitrophenyl) carbonate (Fmoc-Val-Cit-PAB-PNP, 38 mg) was added, followed by DIEA (20 µL). The mixture was stirred at room temperature for 2 h. LC/MS analysis indicated the completion of reaction. Piperidine (50 µL) was added and after 2 h, the reaction mixture was neutralized by addition of acetic acid (200 µL). The crude mixture was purified directly by reverse phase HPLC to give compound 5 as a white solid in TFA salt form after lyophilization (48 mg, 80%). MS: m/z 1438.7 (M+H$^+$).

To a stirred solution of compound 5 (16 mg, 10 µmol) in DMF (1 mL) was added N-ε-Maleimidocaproyl oxysuccinimide ester (4 mg), followed by DIEA (4 µL). The mixture was stirred at room temperature for 2 h. The crude reaction mixture was injected to a Prep HPLC column for purification. Compound 6 was obtained a white solid after lyophilization. (12 mg). MS: m/z 1631.8 (M+H$^+$).

Example 2

Preparation of Compound 8

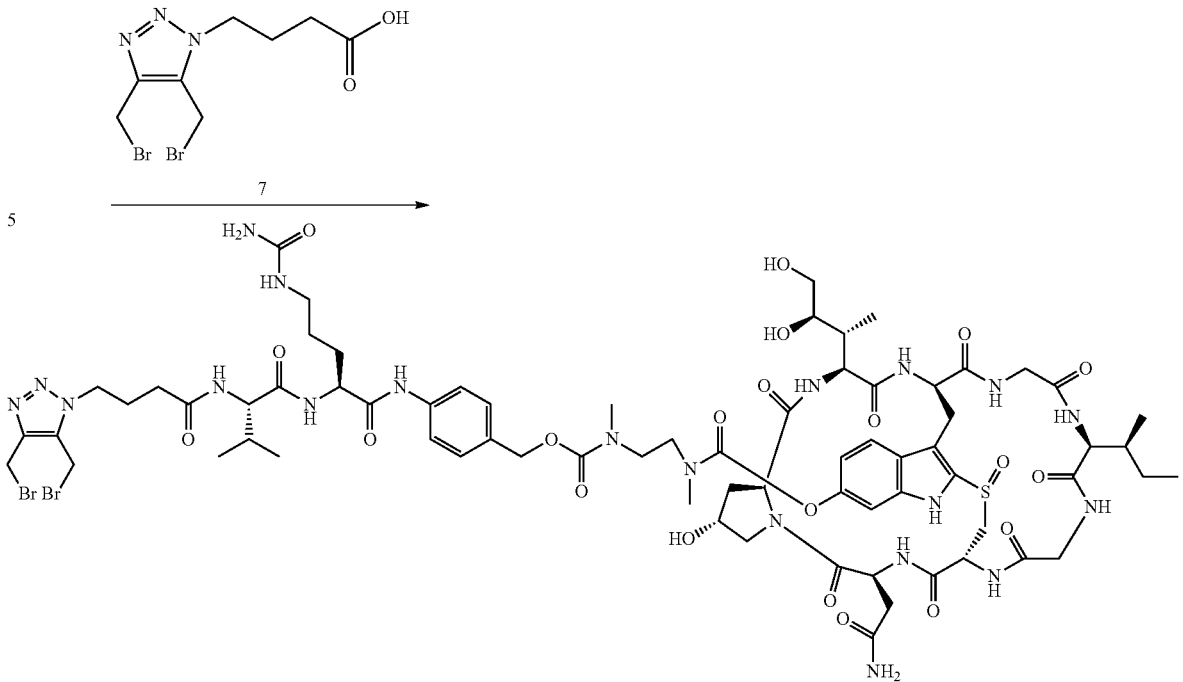

39
To a stirred solution of compound 5 (16 mg, 10 μmol) in DMF (1 mL) was added acid 7 (6 mg), followed by diisopropylcarbodiimide (5 μL). The mixture was stirred at room temperature for 2 h. The crude reaction mixture was injected to a Prep HPLC column for purification. Compound 8 was obtained a white solid after lyophilization. (8 mg). MS: m/z 1761.8 (M+H$^+$).
Example 3
Preparation of Compound 10
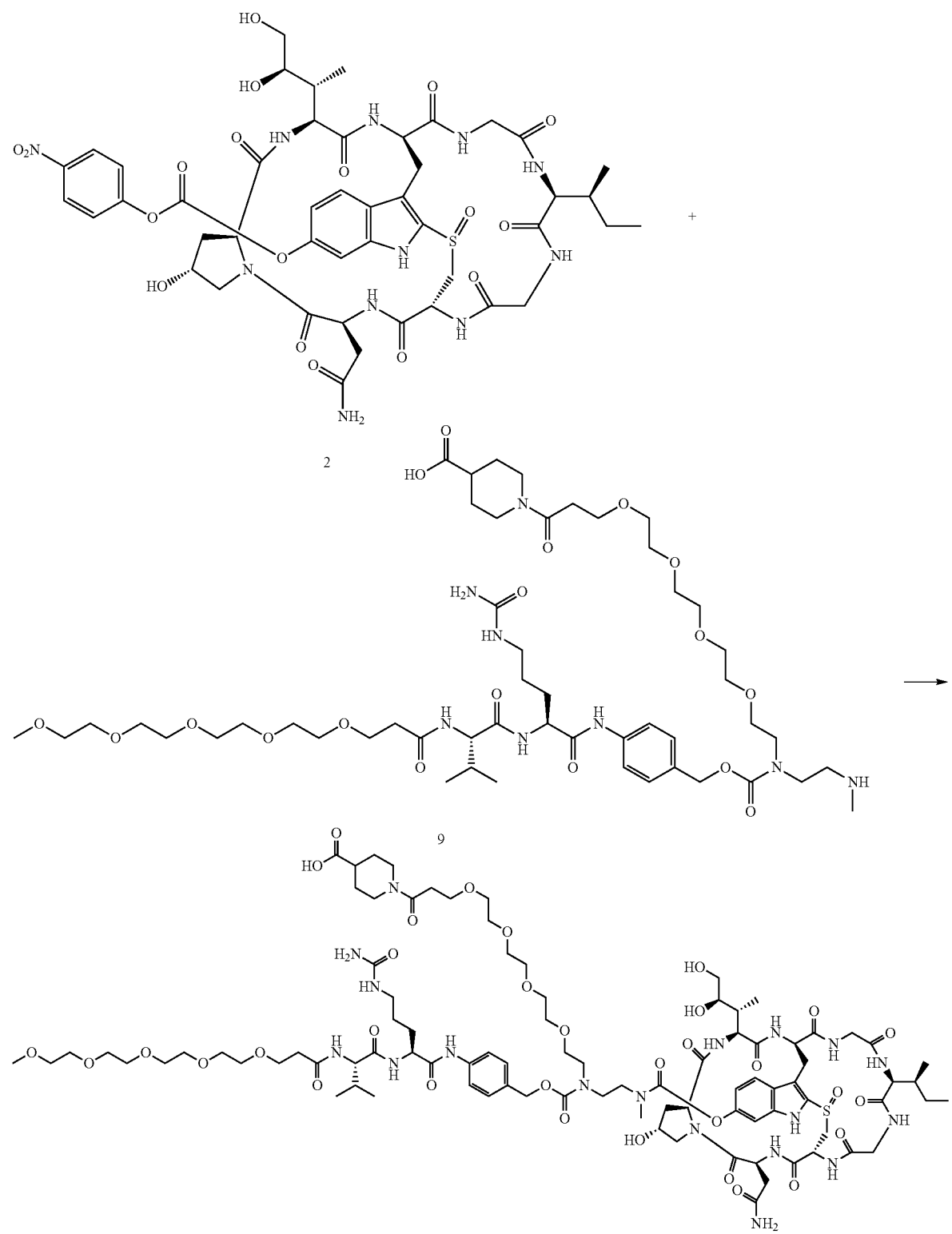

To a stirred solution of compound 2 (30 μmol) in DMSO (1 mL) was added amine 9 (40 mg), followed by DIEA (15 μL). The mixture was stirred at room temperature for 16 h. The crude reaction mixture was injected to a Prep HPLC column for purification. Compound 10 was obtained a white solid after lyophilization. (32 mg). MS: m/z 2046.2 (M+H$^+$).

Compound 10 was converted to the corresponding activated ester following a general procedure prior to conjugating to an antibody.

Example 4

Preparation of Compound 14

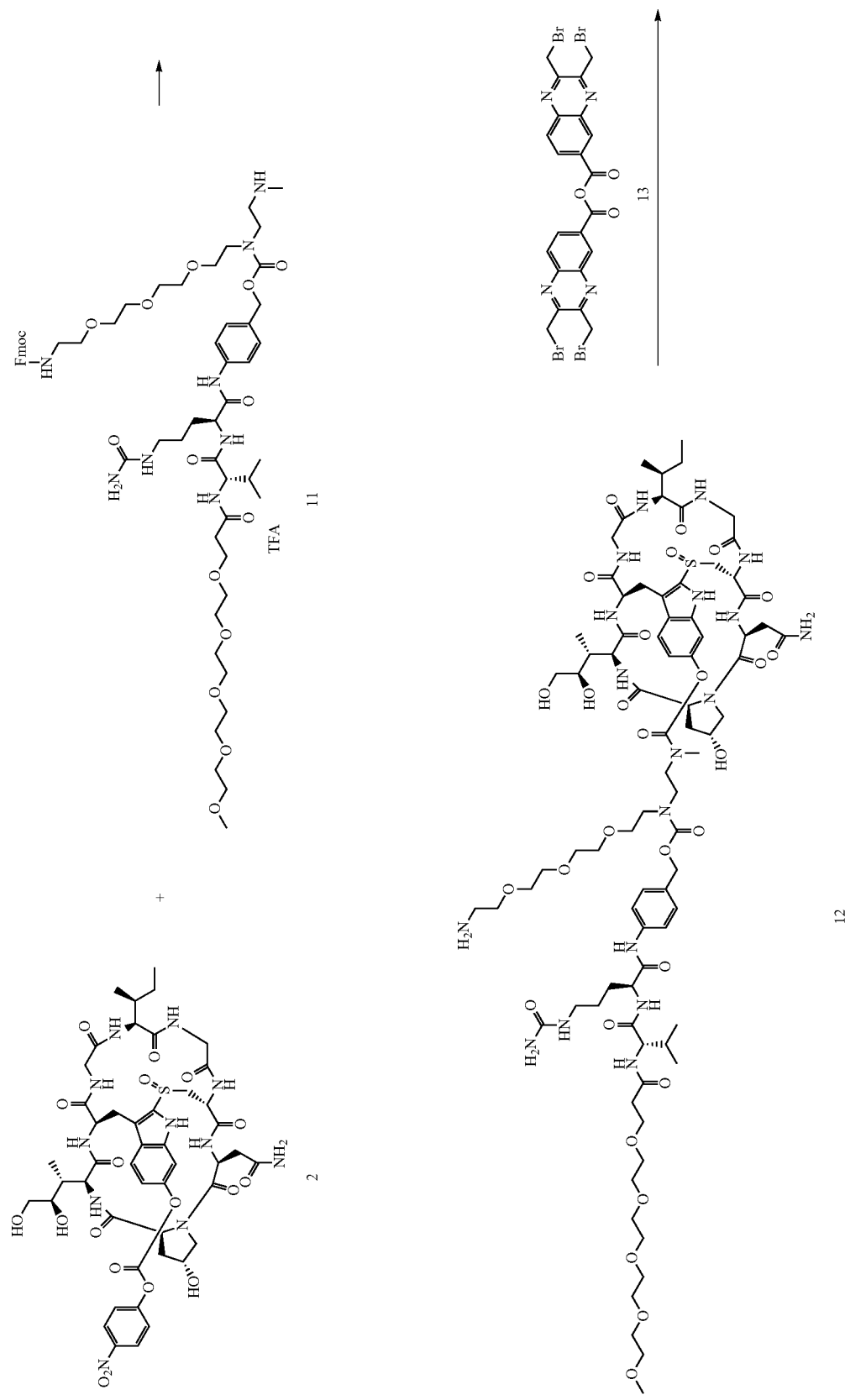

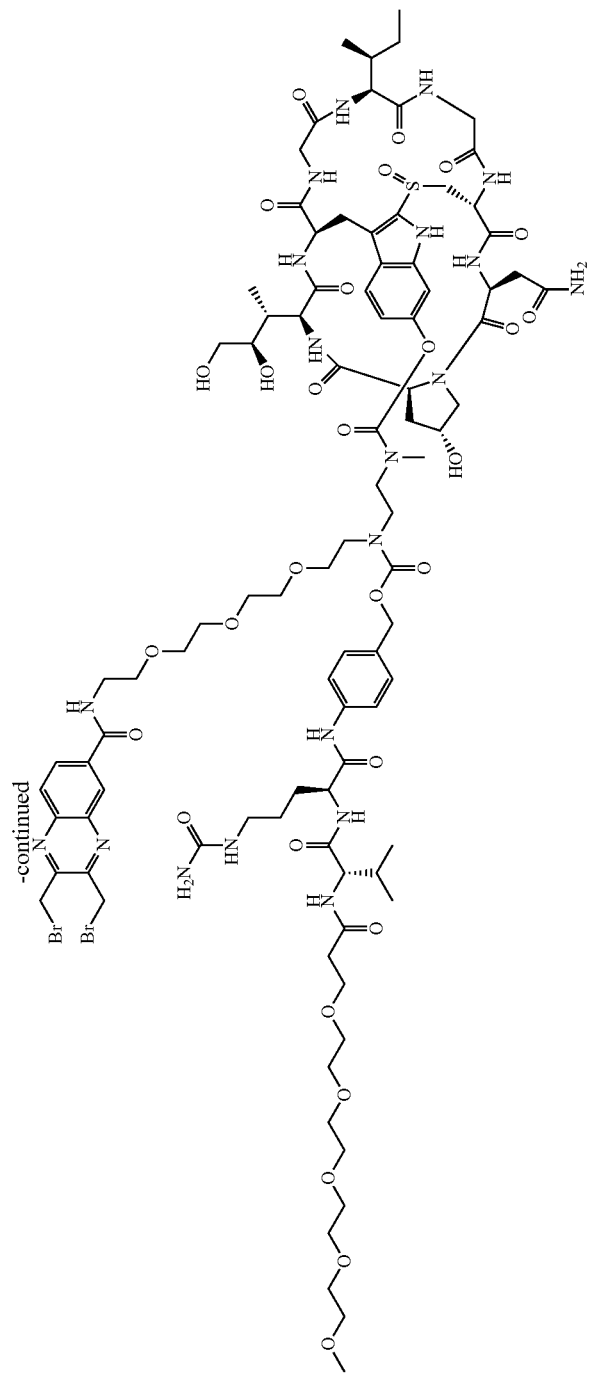
-continued
14

To a stirred solution of compound 2 (50 µmol) in DMSO (1 mL) was added amine 11 (65 mg) in DMF (1 mL), followed by DIEA (20 µL). The mixture was stirred at room temperature for 16 h. Piperidine (100 µL) was added. After 30 mins, the mixture was purified directly by reverse phase HPLC to give compound 12 in TFA salt form as a white solid (54 mg). MS: m/z 1862.1 (M+H$^+$).

Compound 12 (20 mg) was dissolved in DMF (1 mL). Anhydride 13 (11 mg) was added, followed by DIEA (5 µL). The reaction mixture was stirred at room temperature for 5 minutes and purified by reverse phase HPLC to give compound 14 as a white solid after lyophilization (19 mg). MS: m/z 2203.9 (M+H$^+$).

Example 5

Preparation of Compound 17

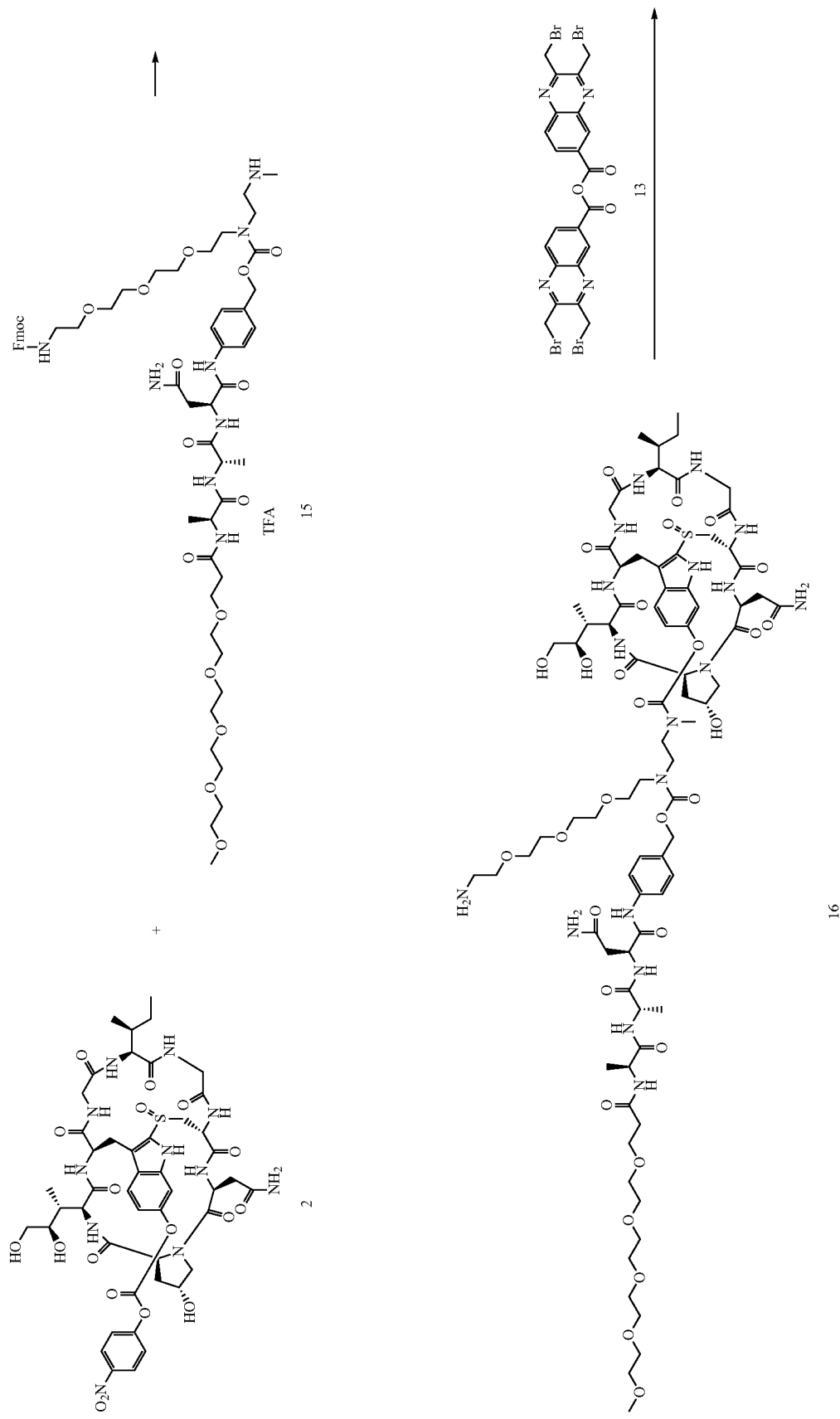

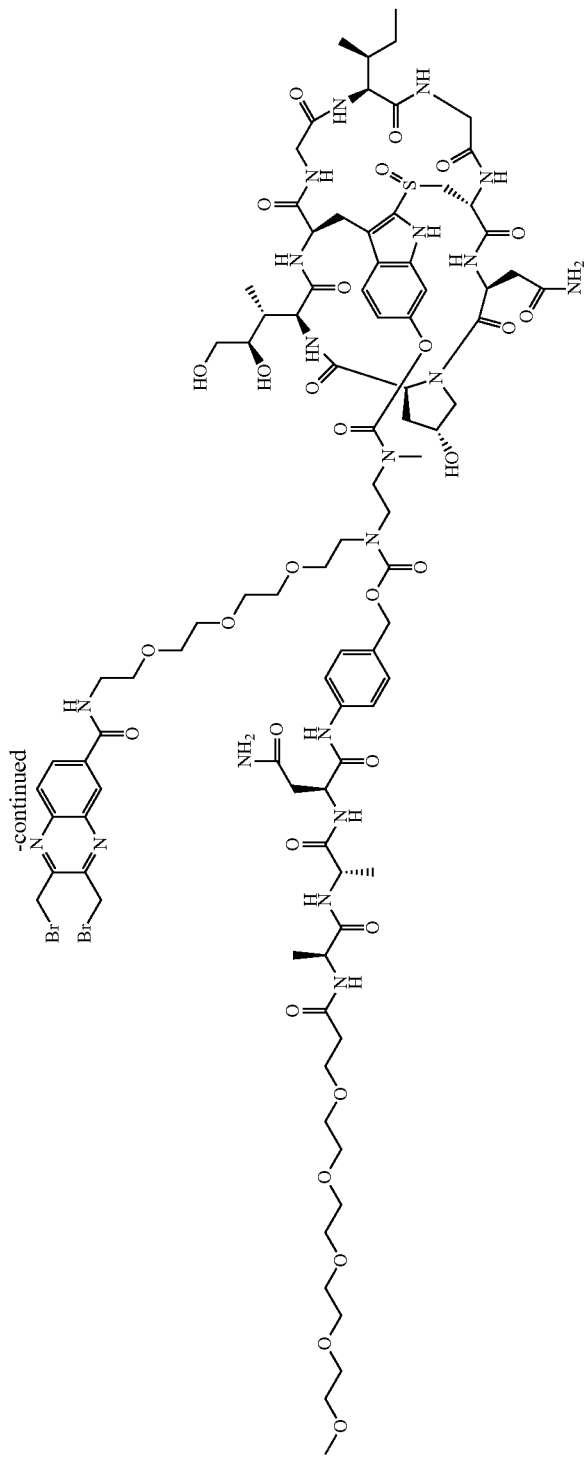

To a stirred solution of compound 2 (50 μmol) in DMSO (1 mL) was added amine 15 (65 mg) in DMF (1 mL), followed by DIEA (20 μL). The mixture was stirred at room temperature for 16 h. Piperidine (100 μL) was added. After 30 mins, the mixture was purified directly by reverse phase HPLC to give compound 16 in TFA salt form as a white solid (49 mg). MS: m/z 1862.3 (M+H$^+$).

Compound 16 (20 mg) was dissolved in DMF (1 mL). Anhydride 13 (11 mg) was added, followed by DIEA (5 μL).

The reaction mixture was stirred at room temperature for 5 minutes and purified by reverse phase HPLC to give compound 17 as a white solid after lyophilization (20 mg). MS: m/z 2204.1 (M+H$^+$).

Example 6

Preparation of Compound 21

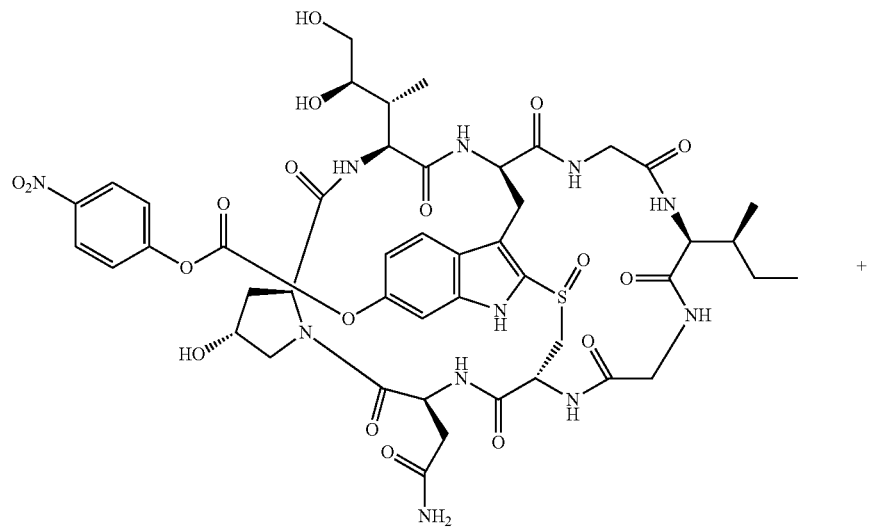

2

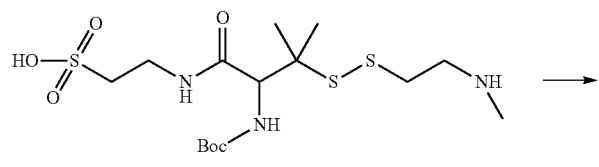

18

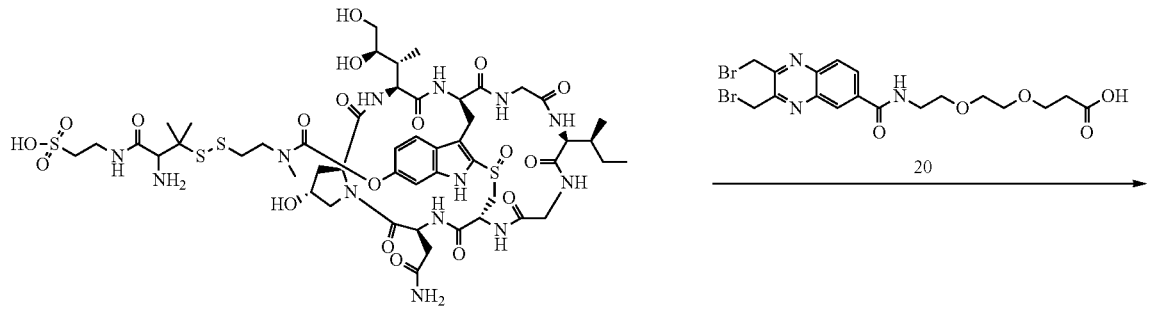

19

-continued

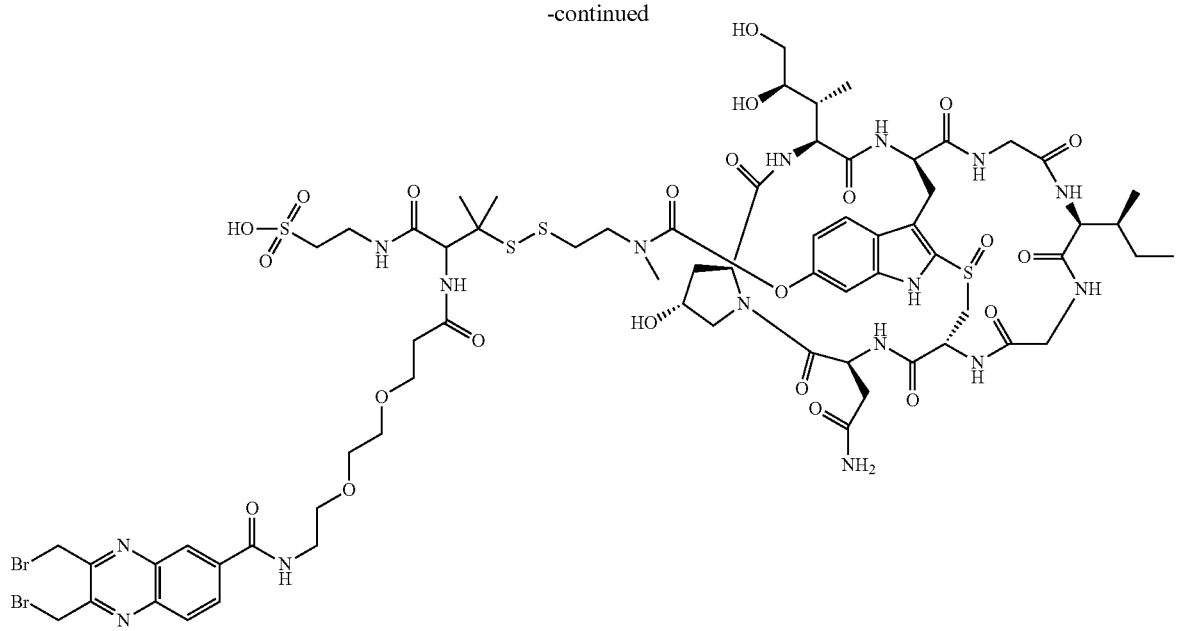

21

To a stirred solution of compound 2 (50 μmol) in DMSO (1 mL) was added amine 15 (25 mg) in DMF (1 mL), followed by DIEA (20 μL). The mixture was stirred at room temperature for 5 h. The solvents were removed under reduced pressure and the residue was dissolved in 20% TFA/DCM (2 mL). After 30 mins, the mixture was purified directly by reverse phase HPLC to give compound 19 as a white solid (31 mg). MS: m/z 1309.5 (M+NH$_4$+).

To a stirred solution of compound 19 (25 mg, 20 μmol) in DMF (1 mL) was added acid 20 (16 mg), followed by diisopropylcarbodiimide (8 μL). The mixture was stirred at room temperature for 2 h. The crude reaction mixture was injected to a Prep HPLC column for purification. Compound 21 was obtained a white solid after lyophilization. (12 mg). MS: m/z 1791.4 (M+H$^+$).

Example 7

Preparation of Compound 28

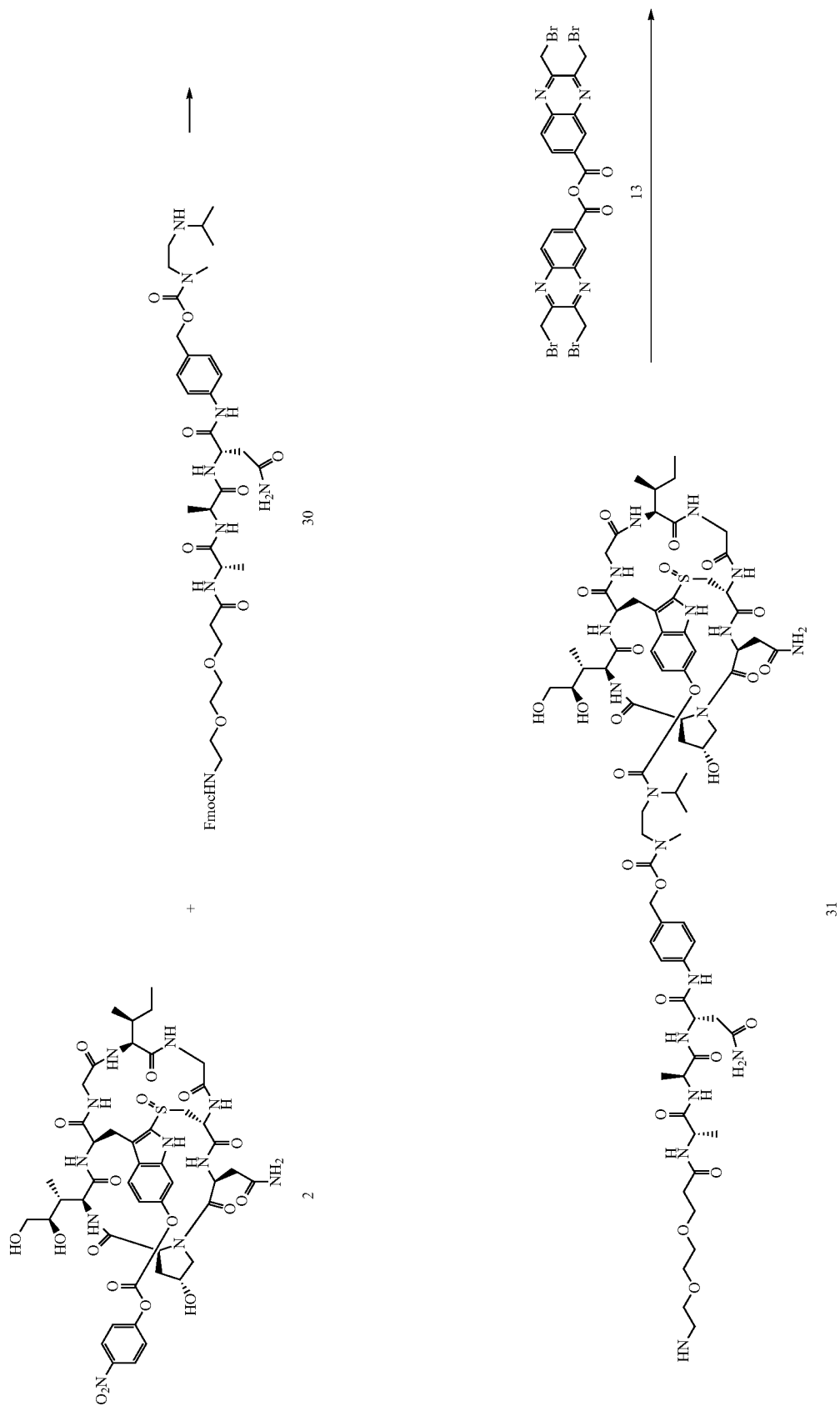

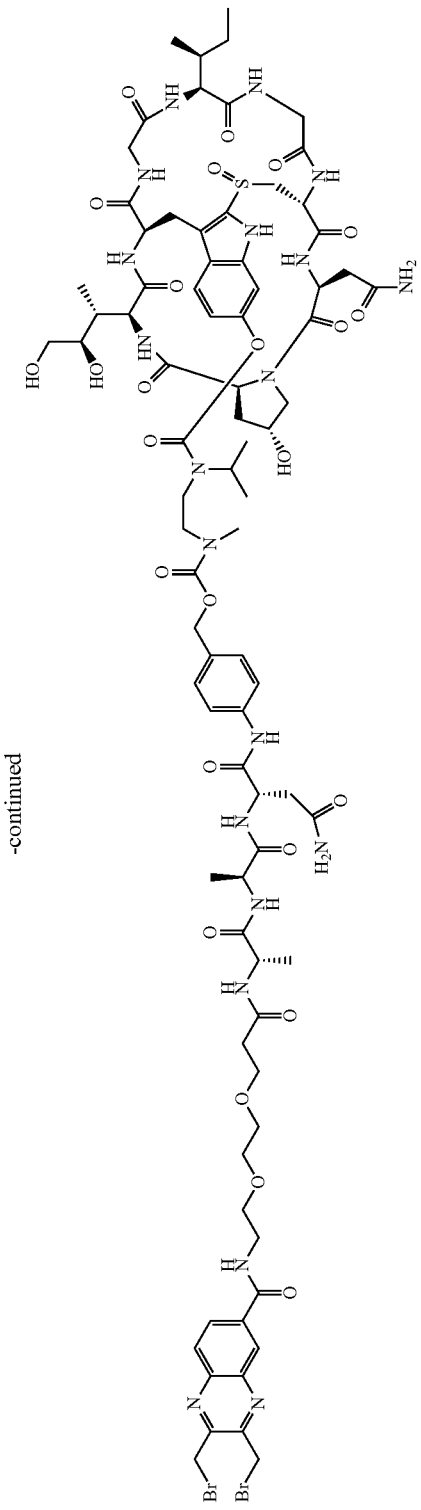

To a stirred solution of compound 2 (50 μmol) in DMSO (1 mL) was added amine 30 (46 mg, 50 μmol) in DMF (1 mL), followed by DIEA (20 μL). The mixture was stirred at room temperature for 16 h. Piperidine (100 μL) was added. After 30 mins, the mixture was purified directly by reverse phase HPLC to give compound 31 in TFA salt form as a white solid (25 mg). MS: m/z 1640.5 (M+H$^+$).

Compound 31 (20 mg, 11.4 μmol) was dissolved in DMF (1 mL). Anhydride 13 (8 mg) was added, followed by DIEA (5 μL). The reaction mixture was stirred at room temperature for 5 minutes and purified by reverse phase HPLC to give compound 28 as a white solid after lyophilization (16 mg). MS: m/z 1981.9 (M+H$^+$).

Example 8

This example provides a comparative study, comparing two different amatinin conjugates shown as "A" and "B" below.

(FIG. 1 four panels for four different cell lines. ADC A completely outperformed ADC B in all 4 Her-2 positive cell lines tested.

Example 9

This example provides the results of EC50 assays (nM) of the designated drug conjugated antibodies measured in vitro in specified cells. The antibody used was an anti-HER2 IgG class of antibody. Seven breast cancer cell lines with various level of Her2 expression as indicated with plus or minus signs in the table below were plated in 96 well plate. The ADCs were serial diluted and added onto cells for treatment for 5 days. At the end of the study, cell proliferation was measured by Promega's CellTitreGlo. EC50 (in nM) was determined as the concentration of 50% cell growth inhibition. The selection criteria for a successful compound

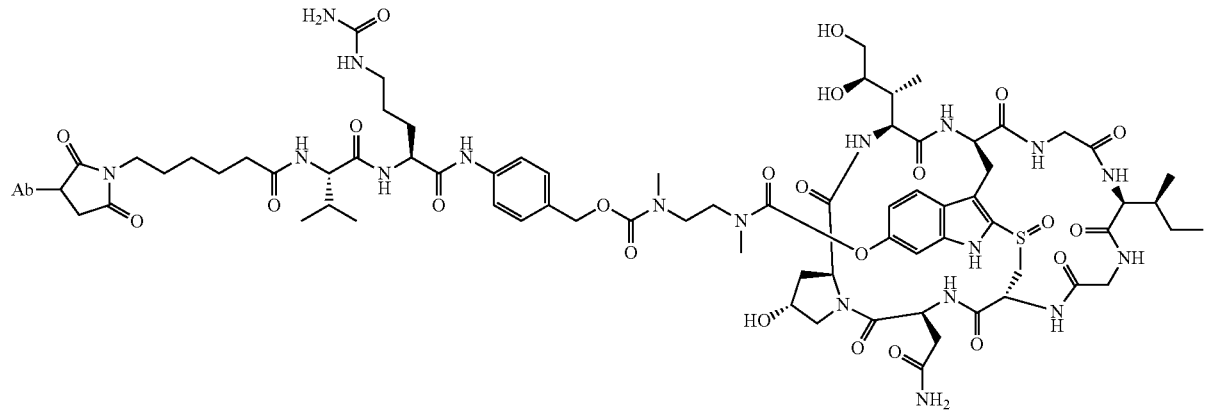

Amanitin Antibody Conjugate Structure A (ADC 22)

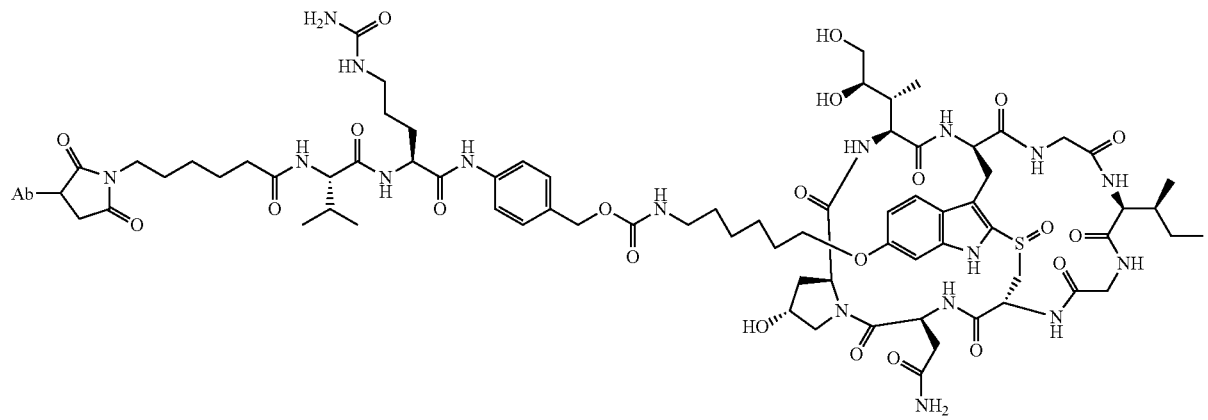

Amanitin Antibody Conjugate Structure B

Figure 2:
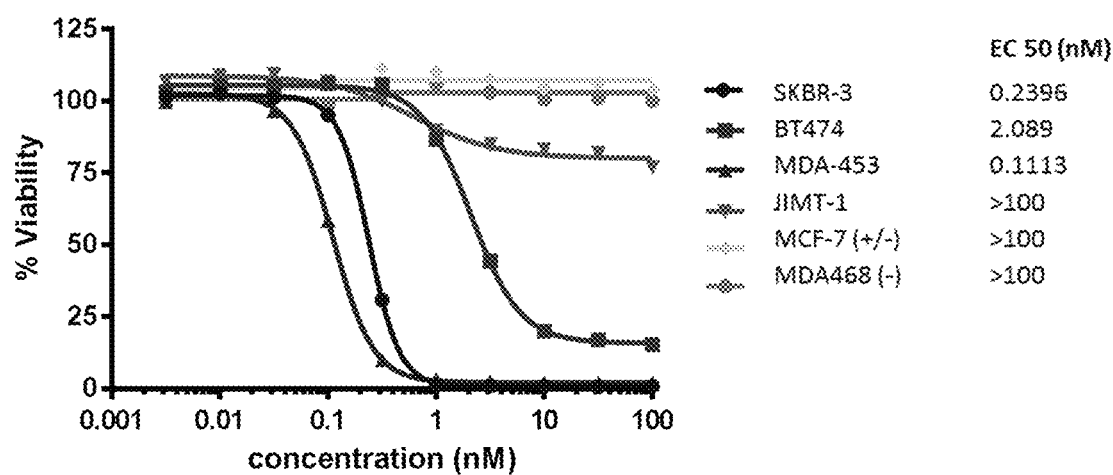
FIG. 2 shows in vitro cytotoxity of ADC24 (see Table 2).
Figure 3:
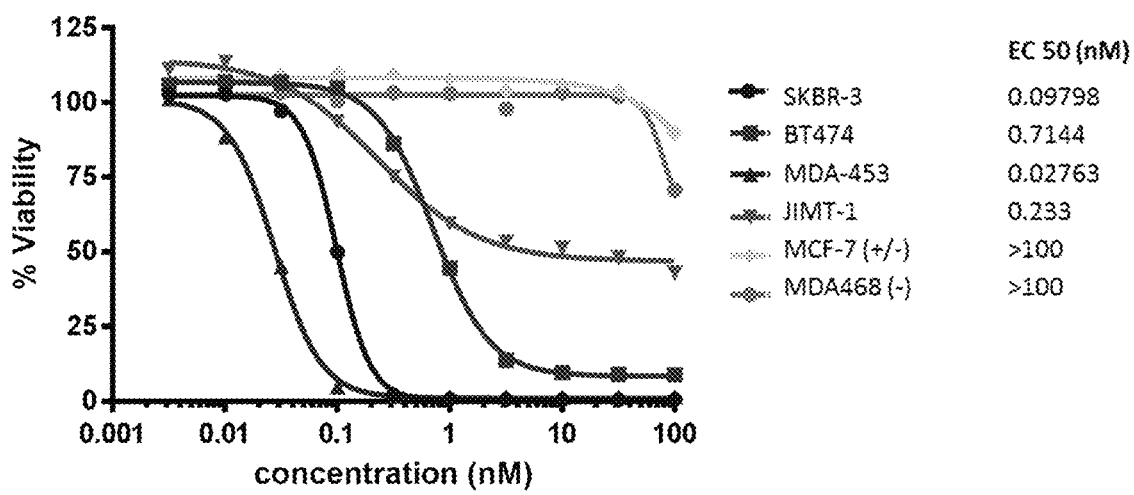
FIG. 3 shows in vitro cytotoxicity of ADC 22 (see Table 2) on various cell lines.

A comparative study was carried out to evaluate the efficacy of amanitin antibody conjugate structure A wherein alpha-amaintin was attached to the linker via a cleavable carbamate bond (reported in this disclosure) and amanitin antibody conjugate structure B wherein alpha amanitin was attached through a non-cleavable ether bond (reported in WO2012/041504) in various in vitro cell killing assays included high efficacy, such as killing cell lines with high expression of the target receptor, with EC50 less than 3 nM. Also, the successful candidate should have low toxicity and good therapeutic window, as determined by relatively low killing of the control cell line (MDA468) with low expression of the target receptor. Both ADCs 22 (FIG. 3) and 24 (FIG. 2) were selected as successful candidates with high efficacy and good therapeutic window.

Example 10

Figure 4:
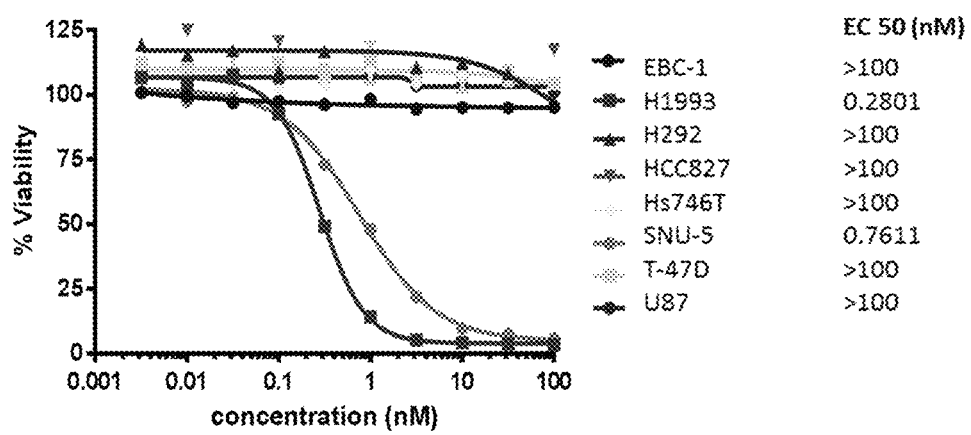
FIG. 4 shows in vitro cytotoxicity of ADC 26 on various cell lines.
Figure 5:
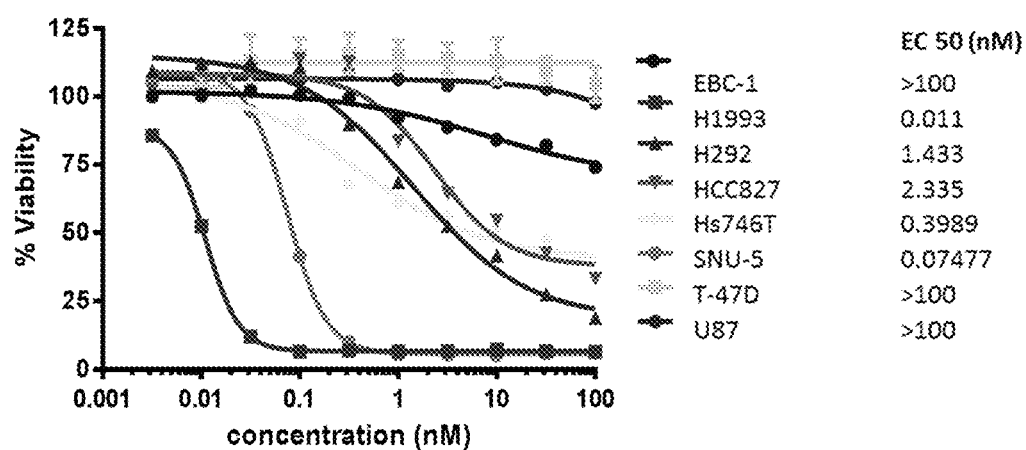
FIG. 5 shows in vitro cytotoxicity of ADC 27 on various cell lines.
Figure 6:
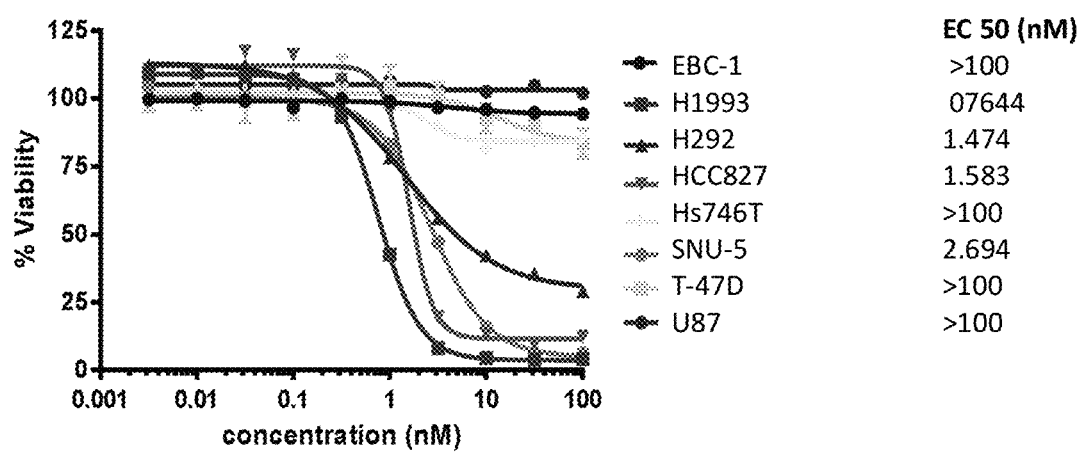
FIG. 6 shows in vitro cytotoxicity of ADC 25 on various cell lines.
Figure 7:
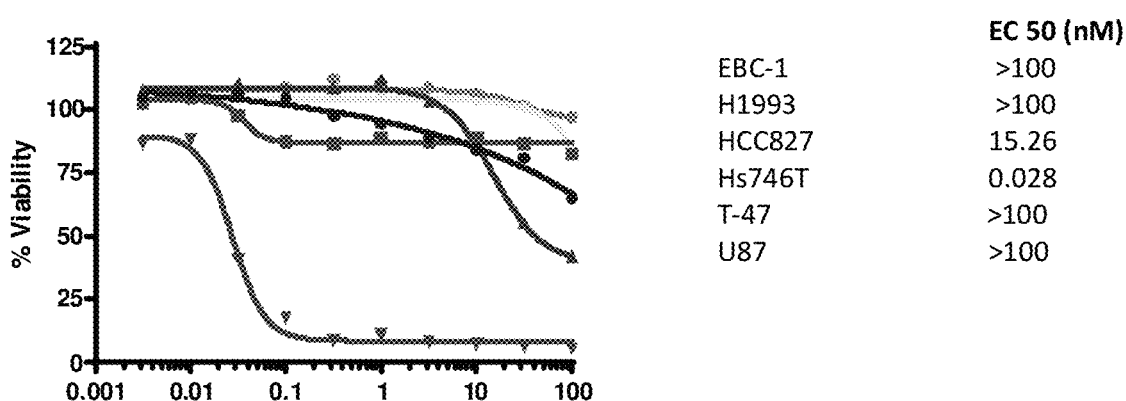
FIG. 7 shows in vitro cytotoxicity of ADC 29 on various cell lines.

This example provides the results of EC50 assays (nM) of designated ADCs described herein measured in vitro in specified cells. The antibody used targets a receptor tyrosine kinase on cell surface. Eight cancer cell lines with various level of receptor expression, as indicated with plus or minus signs in the table below, were plated in 96 well plate. The ADCs were serial diluted and added onto cells for treatment for 5 days. At the end of the study, cell proliferation was measured by Promega's CellTitreGlo. EC50 (in nM) was shown below and determined as the concentration of 50% cell growth inhibition. The selection criteria for a successful compound includes high efficacy, such as killing cell lines with high expression of the target receptor, with EC50 less than 3 nM. Also, the successful candidate should have low toxicity and good therapeutic window, as determined by relatively low killing of the control cell lines (T-47D) with low expression of the target receptor. ADC 25 (FIG. 6) shows good cell killing efficacy in cell lines H1993, HCC827, SNU-5, and H292, but did not show efficacy in Hs746T, EBC-1 and U 87. It showed good therapeutic window since it did not kill the negative control cell line T-47 D. ADC 26 (FIG. 4) shows good cell killing activity in H1993 and SNu-5. However, it is not active in the other 6 cell lines. ADC 27 (FIG. 5) shows excellent cell killing activity in H1993 (EC50=11 pM) and SNu-5 (EC50=75 pM). It also shows good efficacy in Hs746T (EC 50=0.4 nM). ADC 29 (FIG. 7) shows good cell killing efficacy in cell lines Hs746T, but did not show efficacy in EBC-1, U87, HCC827, H1993 and T-47.

Example 11

This example provides the results for the efficacy of ADCs conjugated with small molecule 22, 23, 25, or 27 in a model of H292, HCC827, and H1975 Human Xenograft Tumor Growth in Nude Mice. HCC827, H292, H1975 cell lines were obtained from ATCC. The cells were cultured in RPMI 1640 1X (Corning 10-041-CV) medium with 10% FBS (Seradigm 1500-500) and penicillin streptomycin (Corning 30-002-CI) at 37° C. in a 5% carbon dioxide humidified environment. Cells were cultured for a period of 2 weeks and passaged 4 times before harvest. The cells were harvested with 0.25% trypsin (Corning 25-050-CI). Prior to injection, HCC827 cells were mixed in a 1:1 ratio of HBSS (Hank's balanced salt solution; Ward's 470180-784) and matrigel (Corning 354234) mixture, and 7 million cells per 0.2 ml were injected subcutaneously into the upper right flank of each mouse. H292 cells were resuspended in HBSS, and 5 million cells per 0.2 ml were injected subcutaneously into the upper right flank of each mouse. H1975 cells were resuspended in HBSS, and 3 million cells per 0.2 ml were injected subcutaneously into the upper right flank of each mouse.

Female Nu/Nu mice aged 5-7 weeks (Charles River) were used throughout these studies.

Upon receipt, mice were housed 5 mice per cage in a room with a controlled environment. Rodent chow and water was provided ad libitum. Mice were acclimated to laboratory conditions for 72 hours before the start of dosing. The animals' health status was monitored during the acclimation period. Each cage was identified by group number and study number, and mice were identified individually by ear tags.

The study design and dosing regimens are shown in Table 3.

TABLE 3

| Tumor model | Groups | Animals per Group | Treatment volume/ route | Dose/ Frequency |
| --- | --- | --- | --- | --- |
| H292 | 1 | 7 | PBS | 200 μl/i.v. | 0 mg/kg, single dose |
|  | 2 | 7 | cMet/EGFR-22 | 200 μl/i.v. | 3 mg/kg, single dose |
|  | 3 | 7 | cMet-22 | 200 μl/i.v. | 3 mg/kg, single dose |
|  | 4 | 7 | Nimo-22 | 200 μl/i.v. | 3 mg/kg, single dose |
| HCC827 | 1 | 7 | PBS | 200 μl/i.v. | 0 mg/kg, single dose |
|  | 2 | 7 | cMet/EGFR-23 | 200 μl/i.v. | 3 mg/kg, single dose |
|  | 3 | 7 | cMet-23 | 200 μl/i.v. | 3 mg/kg, single dose |
|  | 4 | 7 | Nimo-23 | 200 μl/i.v. | 3 mg/kg, single dose |
| H1975 | 1 | 8 | PBS | 200 μl/i.v. | 0 mg/kg, single dose |
|  | 2 | 8 | cMet/EGFR-25 | 200 μl/i.v. | 1 mg/kg, single dose |
|  | 3 | 8 | cMet/EGFR-25 | 200 μl/i.v. | 3 mg/kg, single dose |
| HCC827 | 1 | 8 | PBS | 200 μl/i.v. | 0 mg/kg, single dose |
|  | 2 | 8 | cMet-27 | 200 μl/i.v. | 0.3 mg/kg, single dose |
|  | 3 | 8 | cMet/EGFR-27 | 200 μl/i.v. | 1 mg/kg, single dose |
|  | 4 | 8 | cMet/EGFR-27 | 200 μl/i.v. | 3 mg/kg, single dose |

Tumor growth was monitored by measurement of tumor width and length using a digital caliper starting day 5-7 after inoculation, and followed twice per week until tumor volume reached ~100-250 mm$^3$. Tumor volume was calculated using the formula: Volume (mm$^3$)=[Length (mm)×Width (mm)$^2$]/2. Once tumors were staged to the desired volume, animals were randomized, and mice with very large or small tumors were culled. Mice were divided into groups with animal numbers per group as indicated in study design. Mice were then treated intravenously (0.2 ml/animal) with either PBS or antibody conjugated with 22, 23, 25, or 27 as dose indicated in study design. Tumor growth was monitored, and each group of mice was sacrificed when the average tumor load for the control group exceeded 2000 mm$^3$.

Tumor volume was measured twice weekly throughout the experimental period to determine TGI (tumor growth inhibition %). The body weight of each mouse was measured twice weekly by electric balance. Group average and standard deviation were calculated, and statistical analyses (one-way ANOVA with Dunnett's multiple comparison test; GraphPad Prism 6.0) was carried out. All treatment groups were compared with the PBS group. $P<0.05$ was considered statistically significant.

Figure 8:
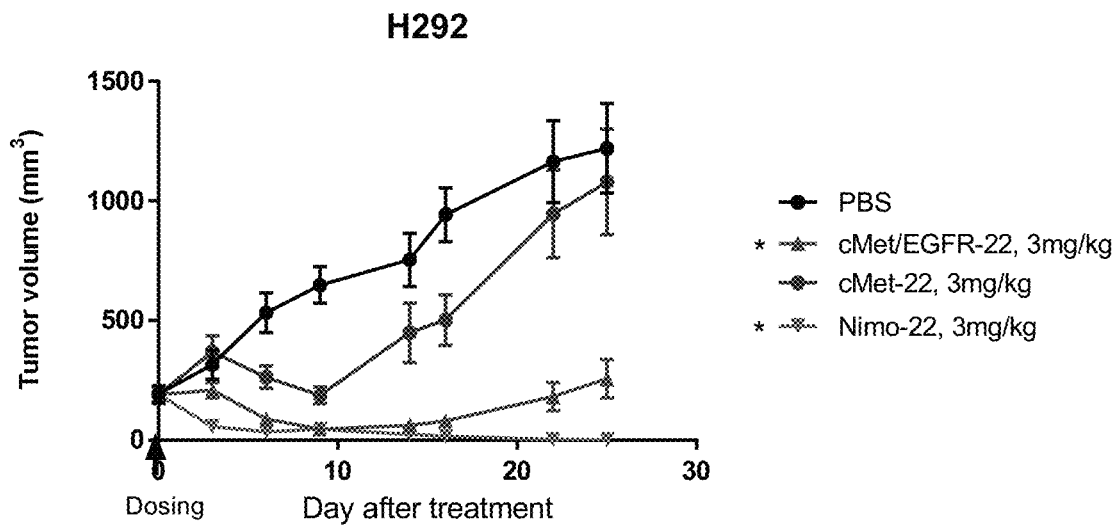
FIG. 8 shows efficacy of cMet/EGFR-22, cMet-22 and Nimo-22 in H292 xenograft: cMet/EGFR-22 and Nimo-22 significantly inhibited H292 tumor growth compared to PBS control group.
Figure 9:
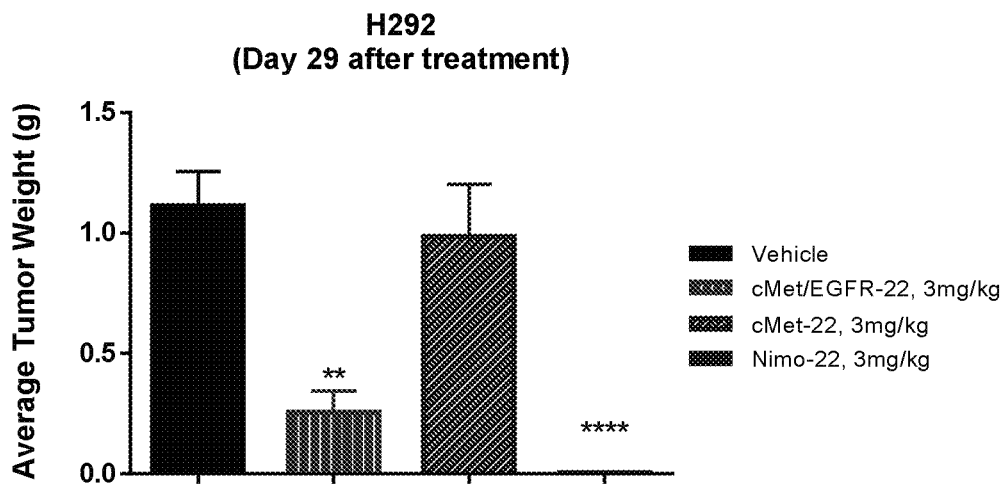
FIG. 9 shows a tumor size comparison for compound 29. cMet/EFFR-22 and Nimo-22 significantly reduced tumor size/Weight compared to PBS Control group. Nimo-22 had some complete tumor regression (4 out of 7 mice was tumor free).
Figure 10:
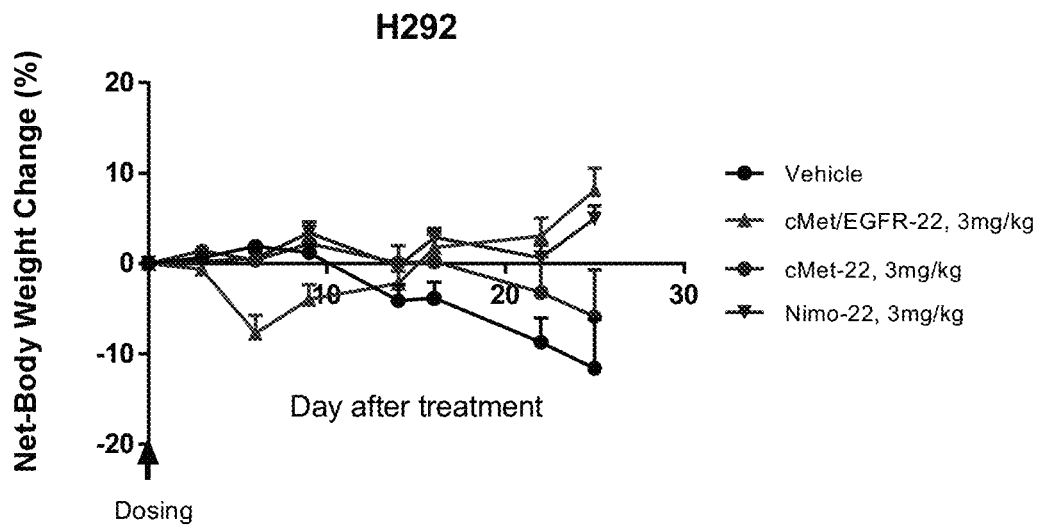
FIG. 10 shows no significant cMet/EGFR-22, cMet-22, Nimo-22 treatment-related body weight loss was observed.
Figure 11:
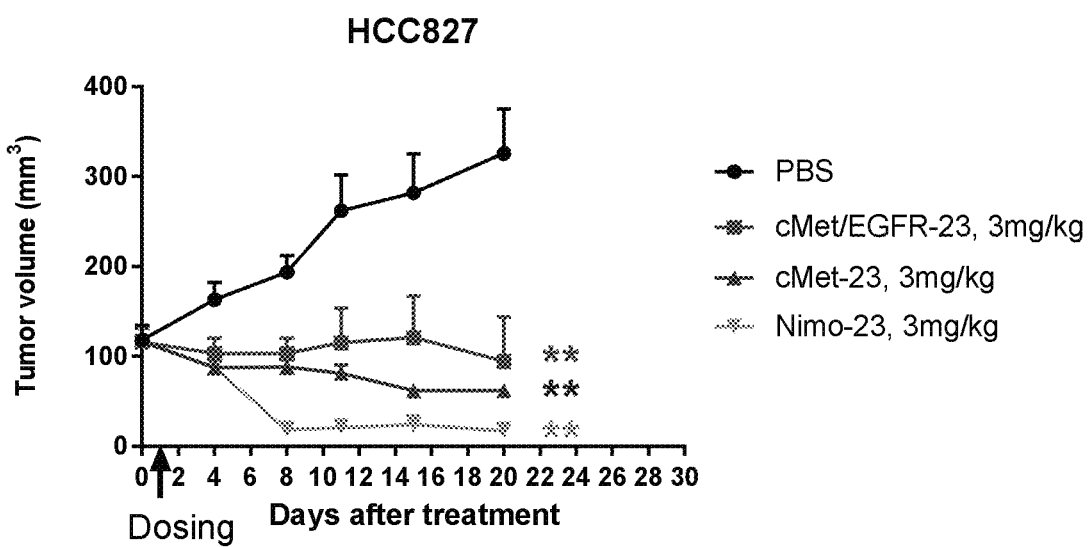
FIG. 11 shows cMet/EGFR-23, cMet-23 and Nimo-23 treated groups showed significantly reduced tumor volume compared to PBS Control group.
Figure 12:
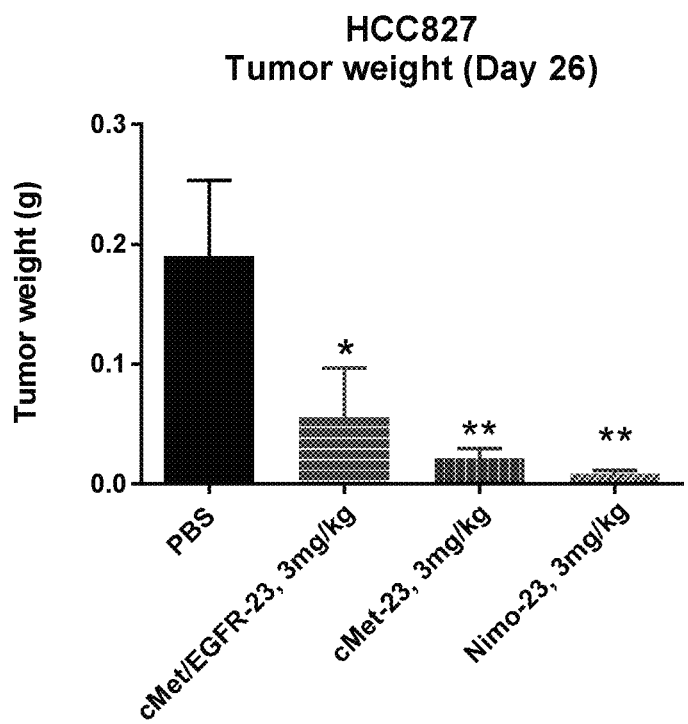
FIG. 12 shows cMet/EGFR-23, cMet-23 and Nimo-23 treated groups showed significantly reduced tumor weight compared to PBS Control group.
Figure 13:
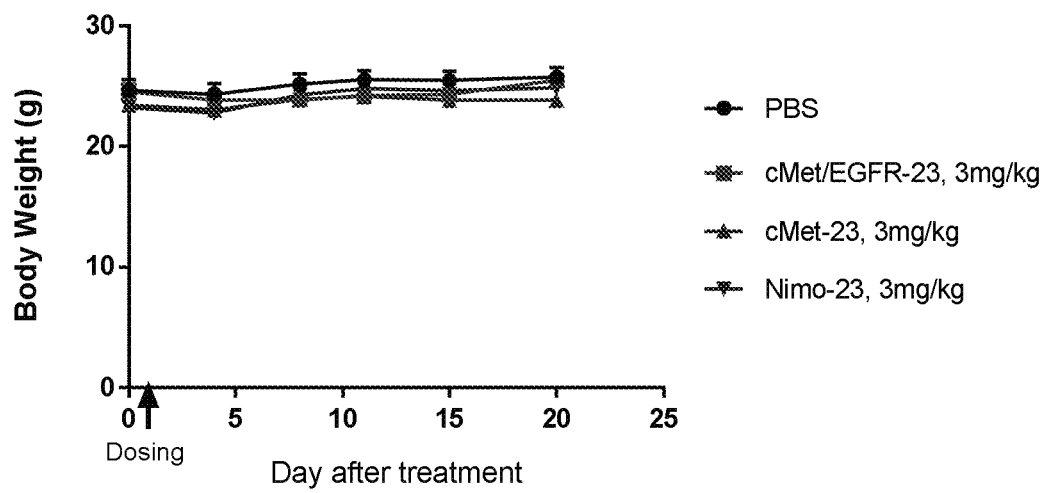
FIG. 13 shows that no body weight loss was observed in cMet-23, cMet/EGFR-23, and Nimo-23 treated group.

A single dose of cMet/EGFR-22 and Nimo-22 treatment at 3 mg/kg significantly inhibited H292 tumor growth when compared to PBS treated control group. While cMet-22 inhibited tumor growth in the first 10 days after treatment, tumor regained growth after 10 days (FIGS. 8 and 9). In this study, a single dose of cMet/EGFR-22 and cMet-22 at 3 mg/kg showed skin rash at 3-6 days after treatment, and dry, flaky skin between day 6 to 14. Those skin issues recovered after day 14. There was no significant treatment-related body weight loss observed during the study. (FIG. 10). Although there was body weight loss during the first week in cMet/EGFR-22 treated group, the weight loss was transient and less than 10% of total body weight. Also, the animals regained weight and was healthier overall compared to PBS treated control group A single dose of cMet/EGFR-23, cMet-23, or Nimo-23 treatment at 3 mg/kg each significantly inhibited H292 tumor growth when compared to PBS treated control group (FIGS. 11 and 12). No body weight loss was observed in cMet-23, cMet/EGFR-23, and Nimo-23 treated group (3 mg/kg) (FIG. 13).

Figure 14:
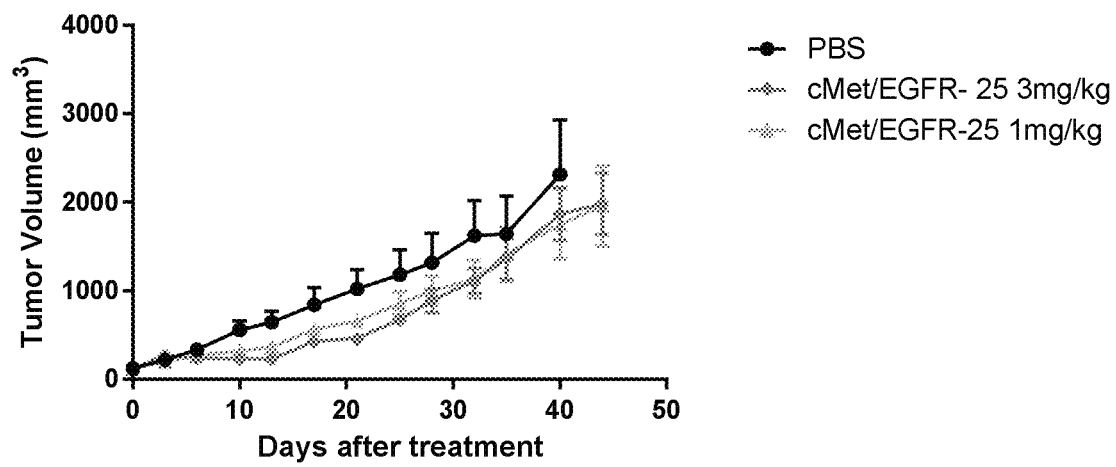
FIG. 14 shows that a single dose of cMet/EGFR-25 at 3 mg/kg or 1 mg/kg had no significant tumor growth inhibition in H1975 xenograft.
Figure 15:
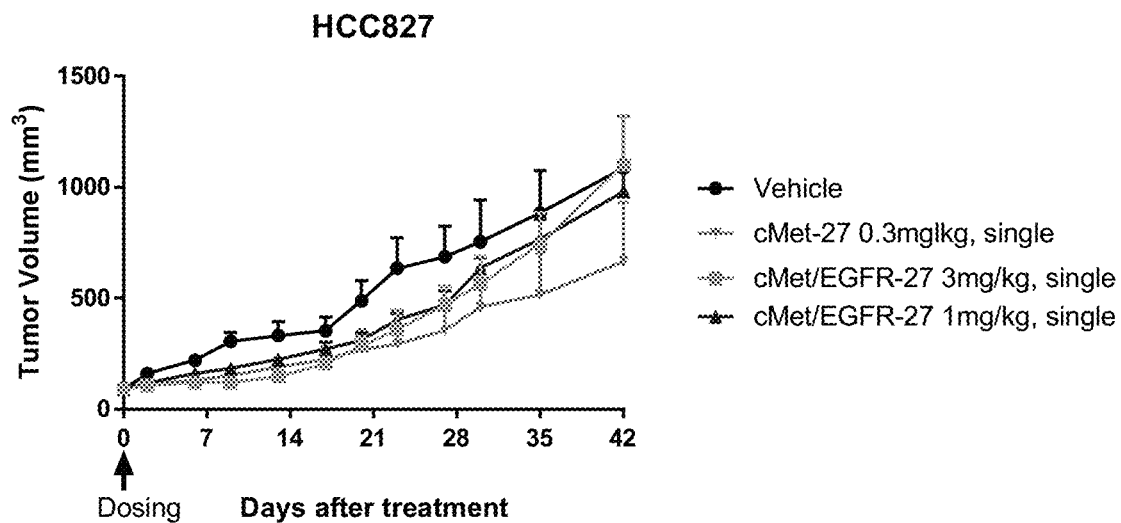
FIG. 15 shows that a single dose of cMet/EGFR-27 at 3 mg/kg or 1 mg/kg, or a single dose of cMet-27 had no significant tumor growth inhibition in HCC827 xenograft.
Figure 16:
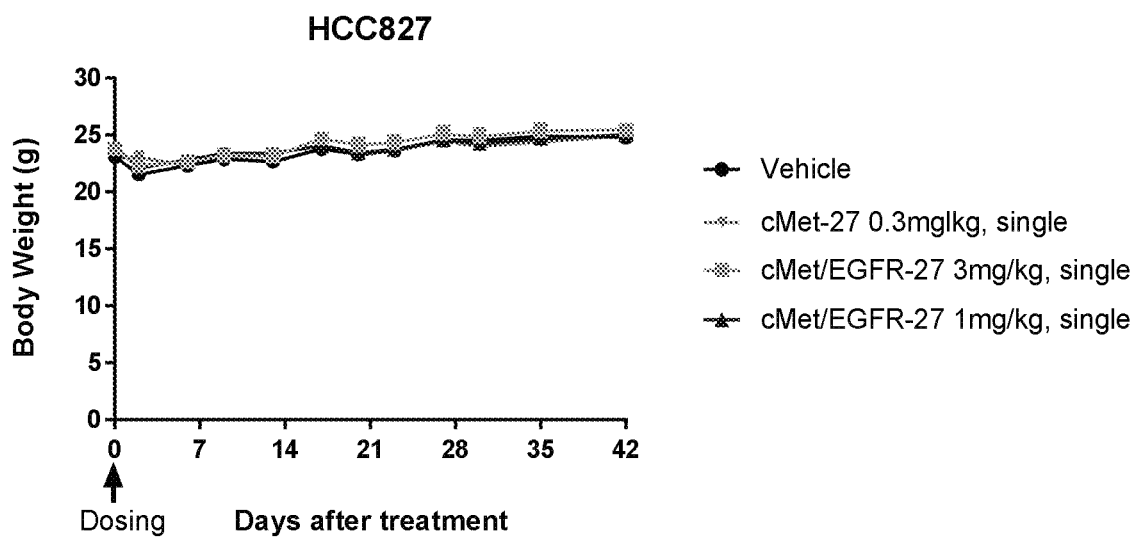
FIG. 16 shows that no significant body weight loss was observed with a single dose of cMet/EGFR-ADC27 at 3 mg/kg or 1 mg/kg, or a single dose of cMet-ADC27 at 0.3 mg/kg during the study.

A single dose of cMet/EGFR-25 at 3 mg/kg or 1 mg/kg had no significant tumor growth inhibition in H1975 xenograft (FIG. 14). A single dose of cMet/EGFR-27 at 3 mg/kg or 1 mg/kg, or a single dose of cMet-27 at 0.3 mg/kg had no significant tumor growth inhibition in HCC827 xenograft (FIG. 15). No significant body weight loss was observed during the study (FIG. 16).

We claim:

1. An antibody drug conjugate (ADC) having the structure of Formula (I):

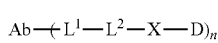

or a pharmaceutically acceptable salt thereof, wherein:

Ab is a monoclonal antibody;

$L^1$-$L^2$ is a linker selected from

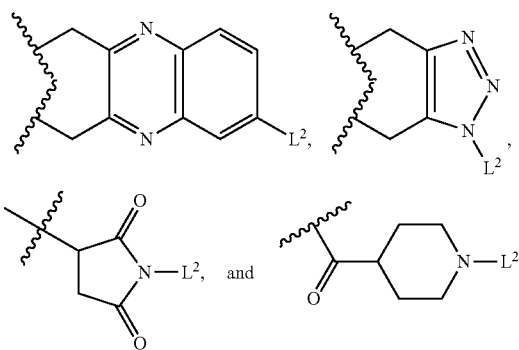

wherein the wavy line indicates the point of attachment to Ab;

$L^2$-X has a structure of

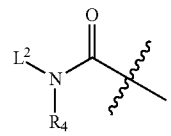

wherein $R_4$ is hydrogen or $C_{1-6}$ alkyl, and the wavy line indicates the point of attachment to D;

$L^2$ is a linker comprising (a) —$R_6OC(O)NR_5$—, and (b) —$(CH_2)_p$—, —$(CH_2CH_2O)_m$—, —C(O)NH—, —NHC(O)—, or a combination of two or more thereof, wherein:

$R_5$ is hydrogen, $C_{1-6}$ alkyl, —$(CH_2)_p$—, —$(CH_2CH_2O)_m$—, or a combination of two or more thereof;

$R_6$ is Val-Cit-PAB or Ala-Ala-Asn-PAB;

wherein —$R_6OC(O)NR_5$— is connected to $L^1$ through $R_5$ or $R_6$;

D is a drug moiety active agent derived from amatoxin having a structure of Formula (II):

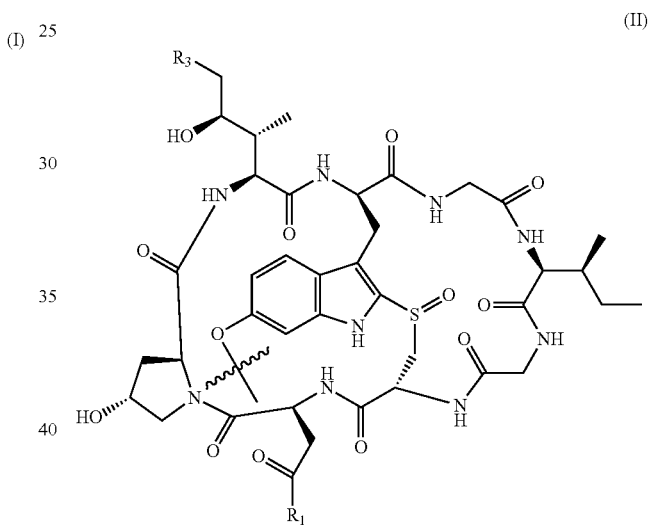

wherein $R_1$ is $NH_2$ or $OR_2$, $R_2$ is H or $C_{1-10}$ alkyl, and $R_3$ is H or OH; and the wavy line indicates the point of attachment to X;

n is an integer from 1-10;

m is an integer from 1-24; and p is an integer from 1-6.

2. The ADC of claim 1, wherein the ADC is selected from the group consisting of:

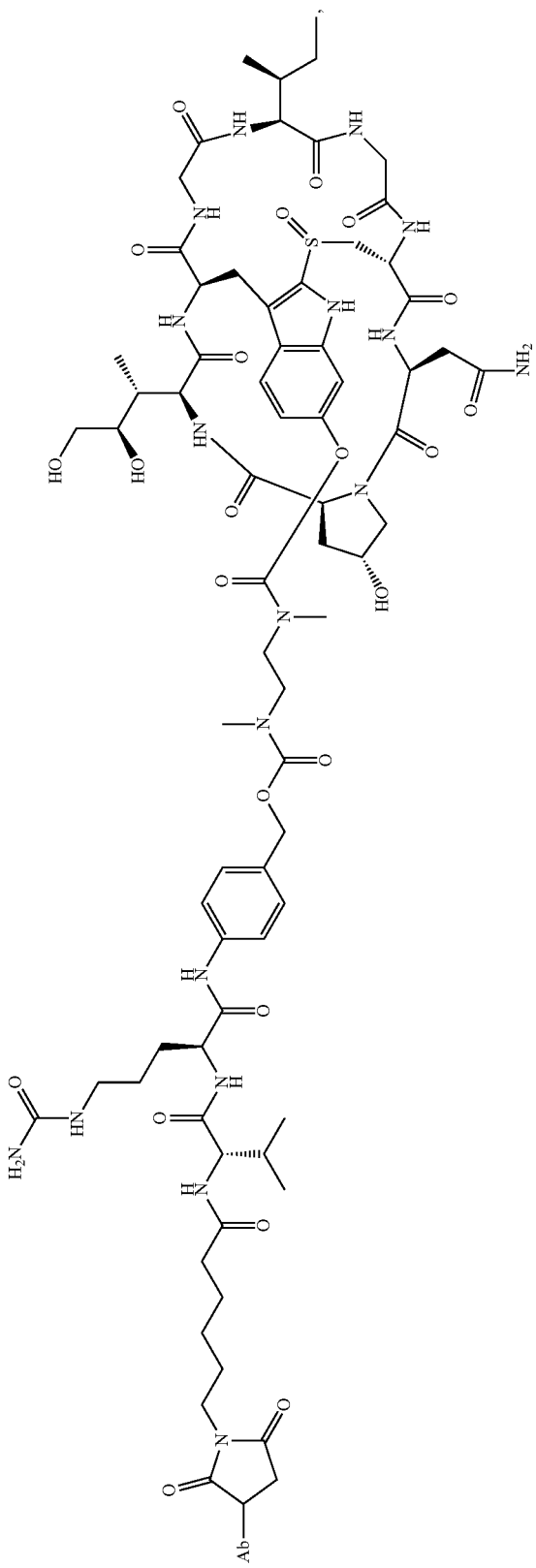

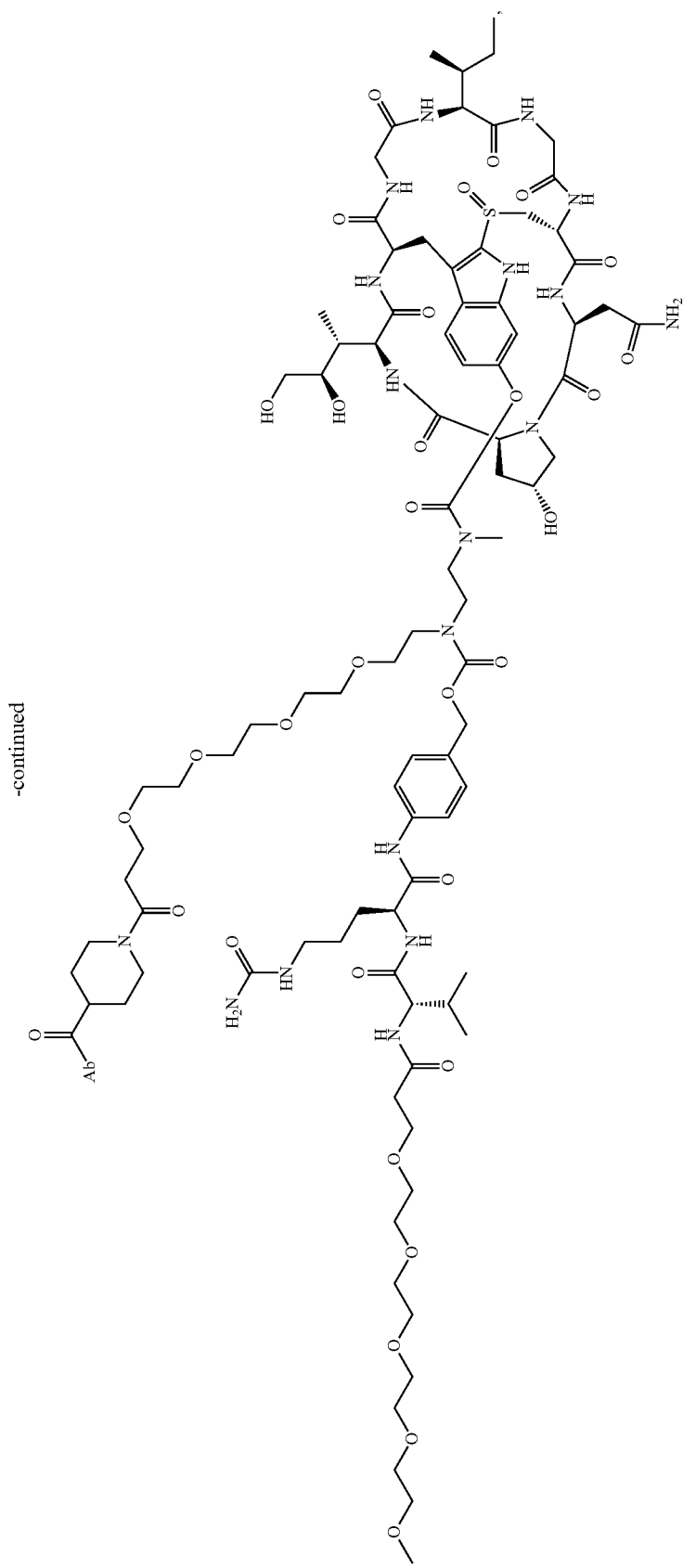

-continued
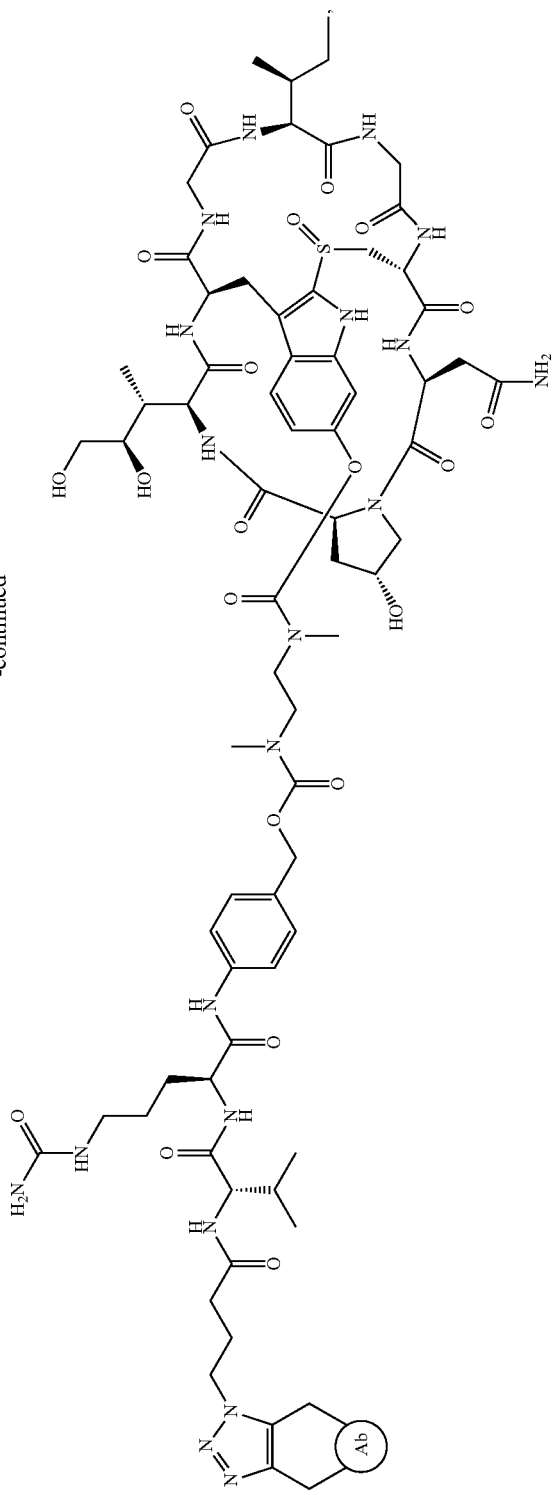

-continued
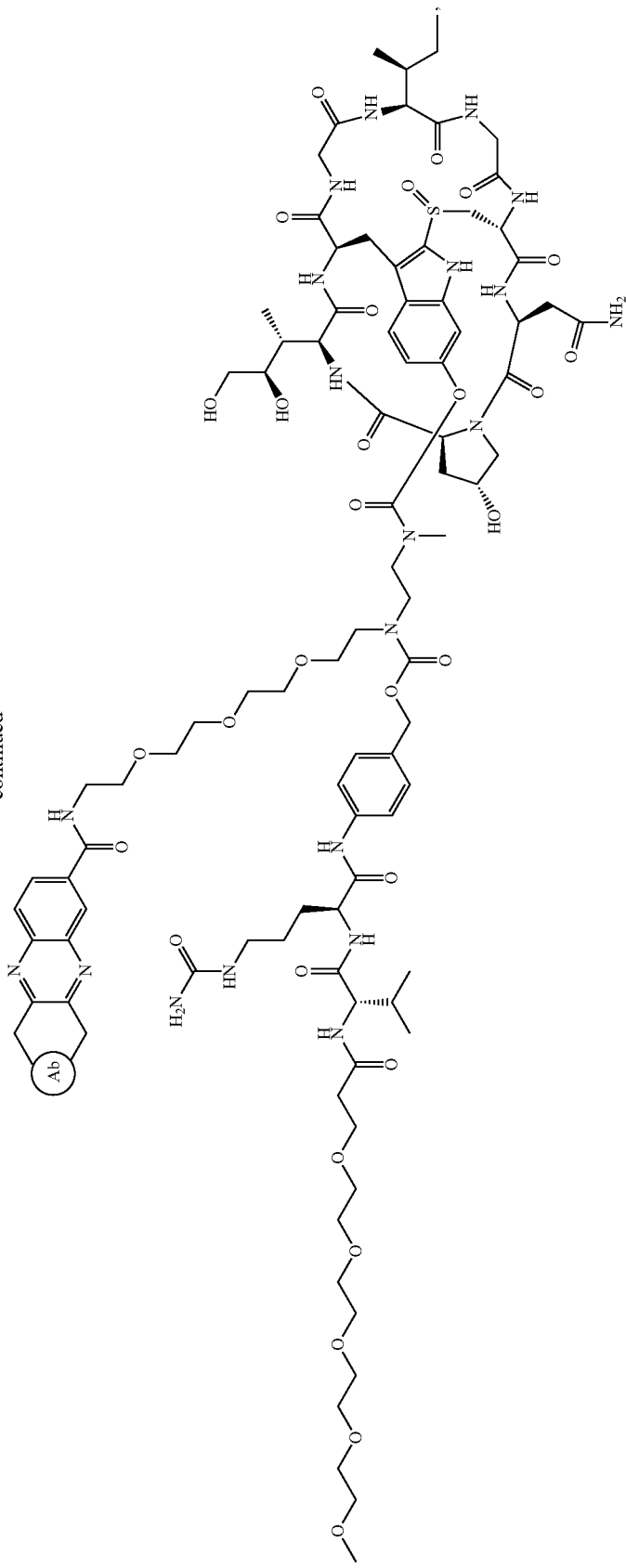

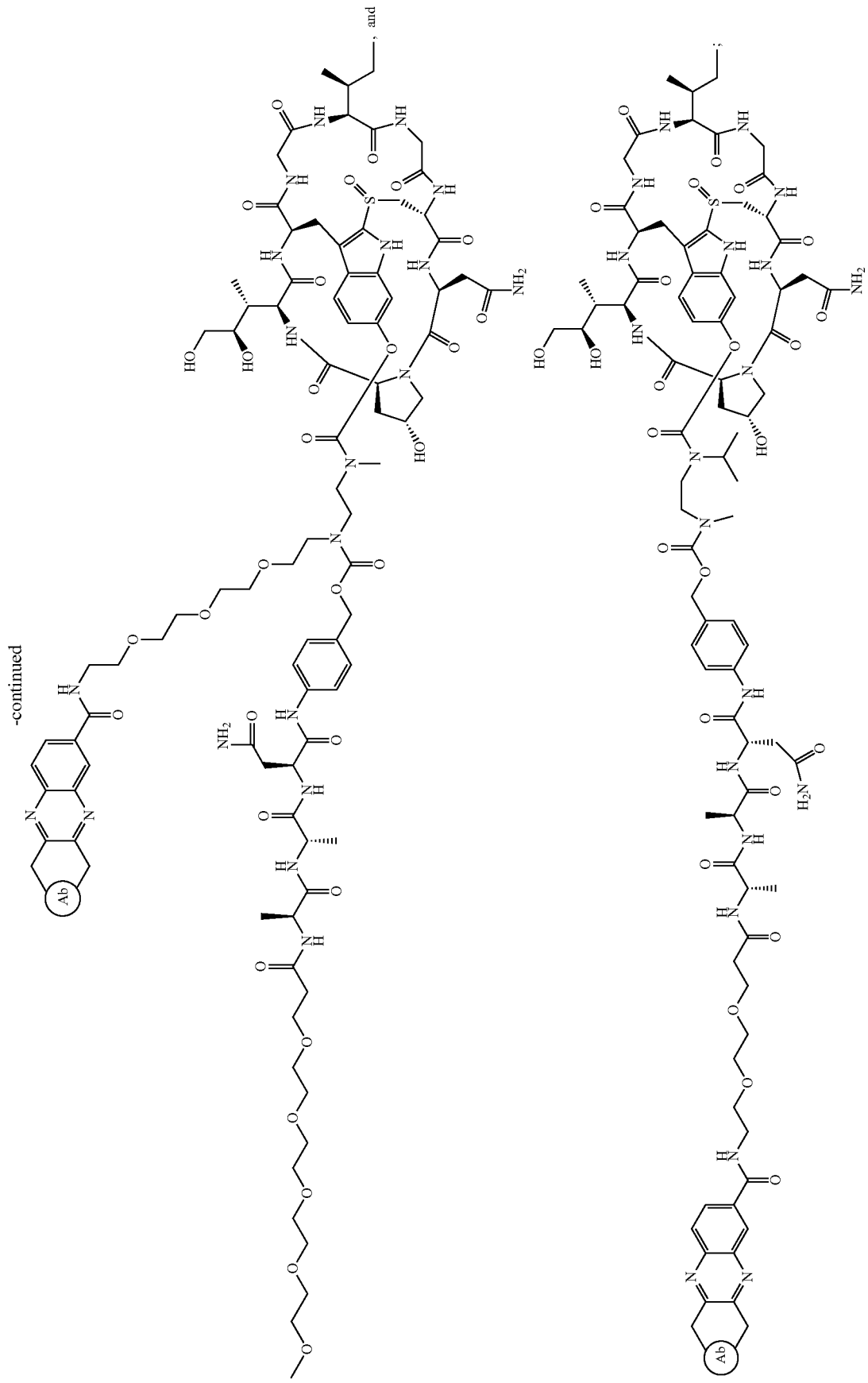

and pharmaceutically acceptable salts thereof.

3. The ADC of claim 1, wherein $R_4$ is $C_{1-6}$ alkyl.

4. The ADC of claim 3, wherein $L^1$-$L^2$ is

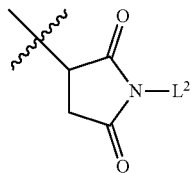

wherein the bond of $L^2$ to X is not shown, and the wavy line indicates the point of attachment of $L^1$ to Ab.

5. The ADC of claim 3, wherein $L^2$ comprises (a) —$R_6$OC(O)$NR_5$— and (b) —(CH$_2$)$_p$—.

6. The ADC of claim 1, wherein n is 1.

7. The ADC of claim 1, wherein $R^6$ is Ala-Ala-Asn-PAB.

8. The ADC of claim 1, wherein $R_5$ is —(CH$_2$)$_p$—.

9. The ADC of claim 1, wherein D has a structure of Formula (II):

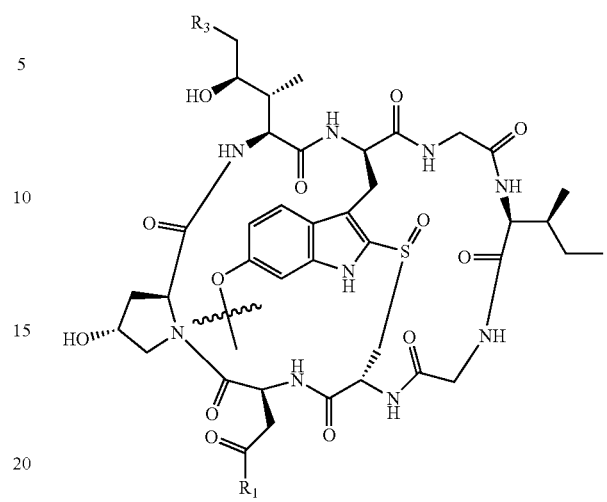

wherein $R_1$ is NH$_2$ or OH, and $R_3$ is H or OH; and the wavy line indicates the point of attachment to X.

10. The ADC of claim 1, wherein $R^6$ is -Val-Cit-PAB-.

11. The ADC of claim 1, wherein $R^4$ is isopropyl.

12. The ADC of claim 1, having the structure of Formula (29)

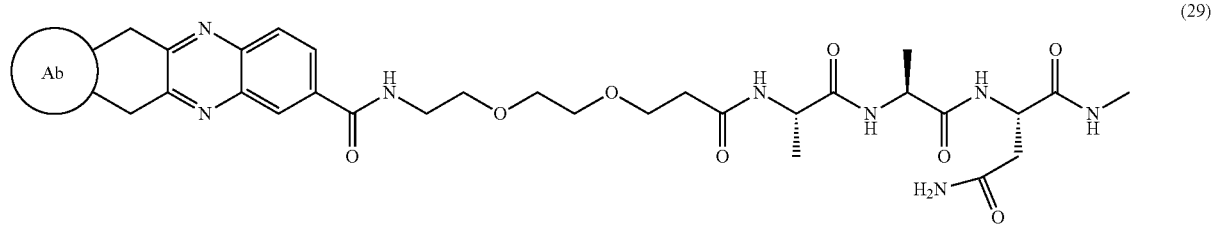

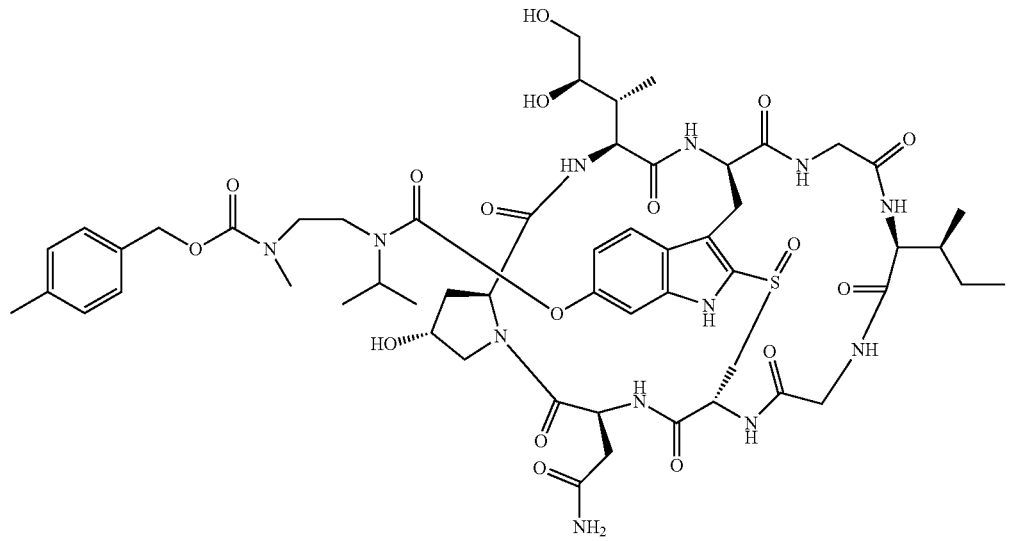

or a pharmaceutically acceptable salt thereof.

13. The ADC of claim 1, wherein $R_5$ is $C_{1-6}$ alkyl.

14. The ADC of claim 13, wherein $R_5$ is methyl.

15. The ADC of claim 3, wherein $R_4$ is methyl.

16. The ADC of claim 1, having the structure
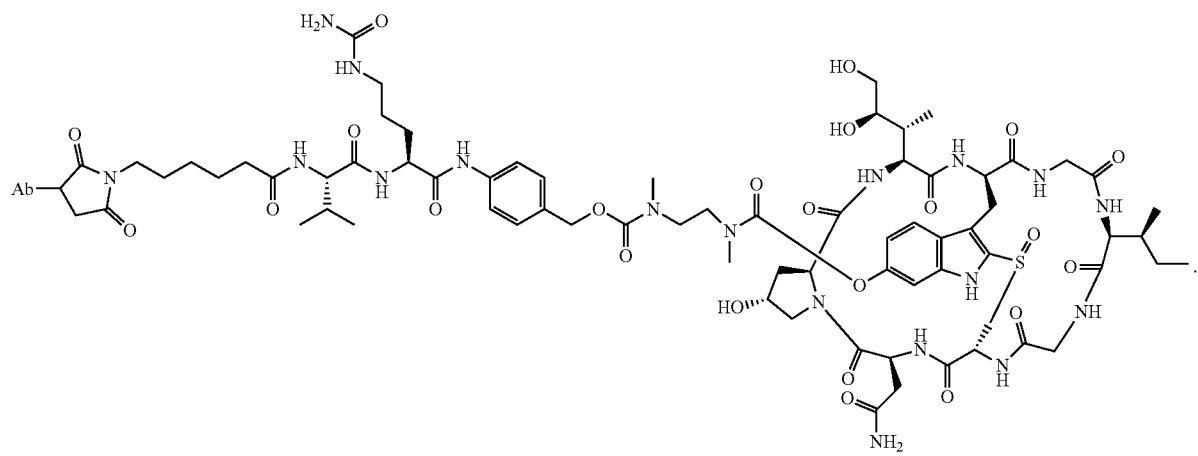
17. The ADC of claim 1, where Ab is an anti-HER2 antibody.
* * * * *